United States Patent
Taki et al.

(10) Patent No.: US 10,415,009 B2
(45) Date of Patent: Sep. 17, 2019

(54) CELL CULTURE DEVICE AND METHOD OF MANUFACTURING THE SAME

(71) Applicants: TOYODA GOSEI CO., LTD., Kiyosu-shi, Aichi-ken (JP); National University Corporation Yamagata University, Yamagata-shi, Yamagata (JP)

(72) Inventors: Seitaro Taki, Kiyosu (JP); Hiroyuki Nakagawa, Kiyosu (JP); Atsuki Yoshimura, Kiyosu (JP); Masaru Tanaka, Yonezawa (JP)

(73) Assignees: TOYODA GOSEI CO., LTD., Aichi-pref. (JP); NATIONAL UNIVERSITY CORPORATION YAMAGATA UNIV., Yamagata-shi (JP)

( * ) Notice: Subject to any disclaimer, the term of this patent is extended or adjusted under 35 U.S.C. 154(b) by 142 days.

(21) Appl. No.: 15/223,387

(22) Filed: Jul. 29, 2016

(65) Prior Publication Data

US 2017/0037353 A1    Feb. 9, 2017

(30) Foreign Application Priority Data

Aug. 4, 2015    (JP) .................. 2015-154078

(51) Int. Cl.
*C12M 3/00*    (2006.01)
*C12M 1/00*    (2006.01)
(Continued)

(52) U.S. Cl.
CPC ............ *C12M 25/02* (2013.01); *B29C 65/02* (2013.01); *B29C 65/08* (2013.01);
(Continued)

(58) Field of Classification Search
CPC ...... C12M 25/02; C12M 25/04; C12M 23/24; C12M 23/26; C12M 25/14
See application file for complete search history.

(56) References Cited

U.S. PATENT DOCUMENTS

| 6,750,039 B1 * | 6/2004 | Bargoot | ............... G01N 1/2813 |
| | | | 422/68.1 |
| 2013/0196368 A1 * | 8/2013 | Moreno | ................. C12M 25/02 |
| | | | 435/34 |

(Continued)

FOREIGN PATENT DOCUMENTS

| CN | 104277236 A | 1/2015 |
| JP | H4-113942 A | 4/1992 |

(Continued)

OTHER PUBLICATIONS http://www.emdmillipore.com/US/en/product/Isopore-Membrane-Filter,MM_NF-TSTP04700 , date unknown.*

(Continued)

*Primary Examiner* — Nathan A Bowers
(74) *Attorney, Agent, or Firm* — Posz Law Group, PLC

(57) ABSTRACT

A cell culture device comprises a cell culture membrane and a substrate fixed to the cell culture membrane. The cell culture membrane is made from a thermosetting resin and has a plurality of pores that are open to at least one surface including a surface on a side that is in contact with the substrate. The substrate is made from a thermoplastic resin. In a contact region between the cell culture membrane and the substrate, part of the substrate is extended to form bulges in the pores of the cell culture membrane that are open in the contact region. This configuration suppresses reduction of the strength of the cell culture membrane and reduction of the flatness of the cell culture membrane (membrane accu- (Continued)

racy) in the cell culture device in which the cell culture membrane and the substrate are fixed to each other.

12 Claims, 14 Drawing Sheets

(51) Int. Cl.
*C12M 1/12* (2006.01)
*B29C 65/00* (2006.01)
*B29C 65/08* (2006.01)
*B29C 65/82* (2006.01)
*B29C 65/02* (2006.01)
*B29K 105/04* (2006.01)
*B29L 31/00* (2006.01)
*B29C 65/14* (2006.01)
*B29C 65/18* (2006.01)

(52) U.S. Cl.
CPC ...... *B29C 65/8223* (2013.01); *B29C 65/8253* (2013.01); *B29C 66/112* (2013.01); *B29C 66/114* (2013.01); *B29C 66/1122* (2013.01); *B29C 66/24221* (2013.01); *B29C 66/304* (2013.01); *B29C 66/30326* (2013.01); *B29C 66/472* (2013.01); *B29C 66/5346* (2013.01); *B29C 66/61* (2013.01); *B29C 66/71* (2013.01); *B29C 66/712* (2013.01); *B29C 66/727* (2013.01); *B29C 66/7392* (2013.01); *B29C 66/7394* (2013.01); *B29C 66/8322* (2013.01); *B29C 66/919* (2013.01); *B29C 66/929* (2013.01); *B29C 66/949* (2013.01); *C12M 23/04* (2013.01); *C12M 25/04* (2013.01); *B29C 65/1412* (2013.01); *B29C 65/18* (2013.01); *B29K 2105/04* (2013.01); *B29L 2031/755* (2013.01); *C12N 2533/30* (2013.01); *C12N 2533/40* (2013.01)

(56) References Cited

U.S. PATENT DOCUMENTS

| | | | |
|---|---|---|---|
| 2015/0017725 A1 | 1/2015 | Taki et al. | |
| 2016/0194588 A1* | 7/2016 | Guenat | C12M 21/08 435/305.1 |
| 2016/0313306 A1* | 10/2016 | Ingber | C12M 21/08 |
| 2017/0181426 A1* | 6/2017 | Wolf | A01N 1/021 |
| 2017/0362554 A1* | 12/2017 | Martin | C12N 5/0602 |

FOREIGN PATENT DOCUMENTS

| | | |
|---|---|---|
| JP | 2006-199063 A | 8/2006 |
| JP | 2011-120504 A | 6/2011 |
| JP | 2013-47030 A | 3/2013 |

OTHER PUBLICATIONS https://shop.pall.com/us/en/laboratory/analytical-qc/mobile-phase-filtration/ptfe-membrane-disc-filters-zidgri7817a, date unknown.*
Office Action dated Apr. 23, 2018 issued in corresponding CN patent application No. 201610624778.9.
Office Action dated Jul. 31, 2018 issued in corresponding JP patent application No. 2015-154078 (and English translation).

* cited by examiner

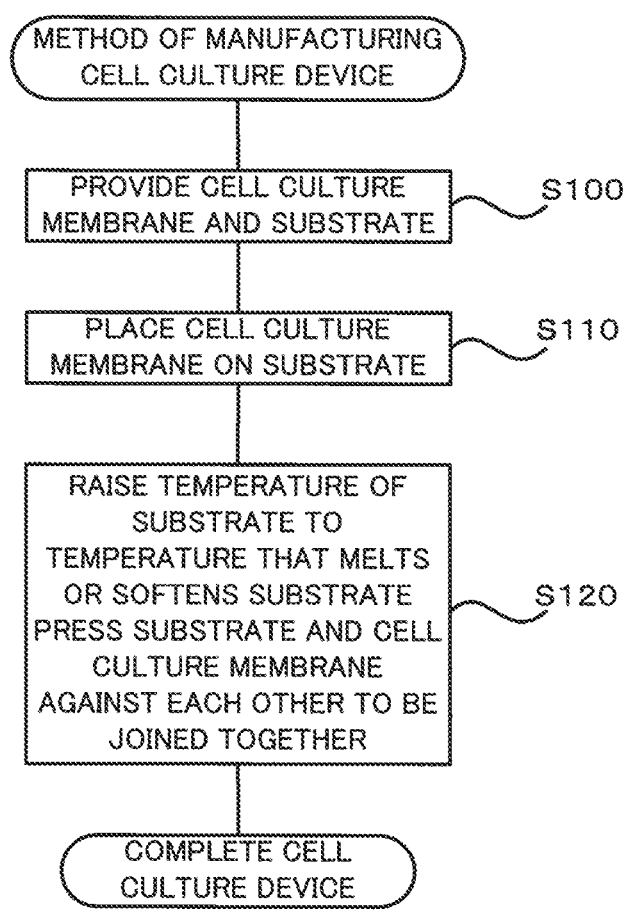

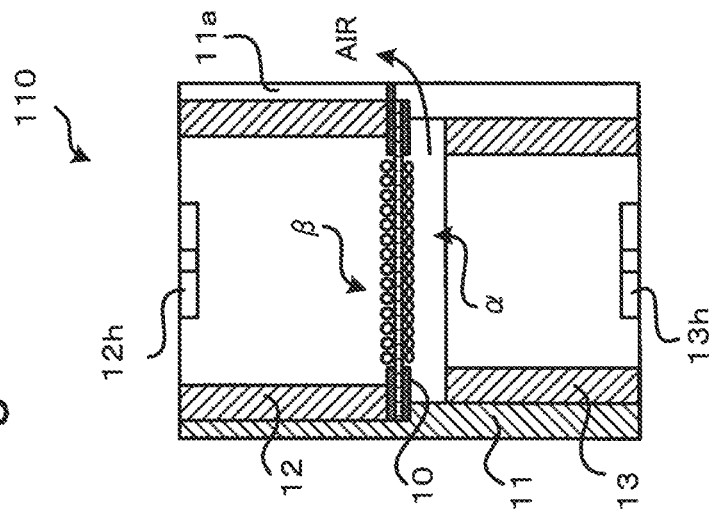
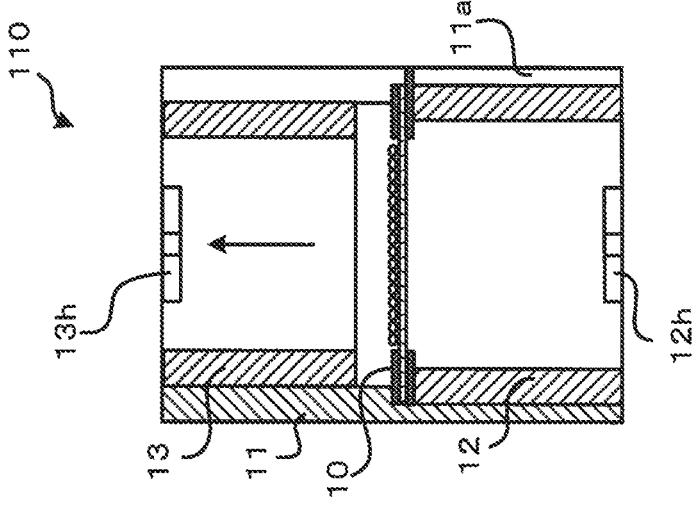
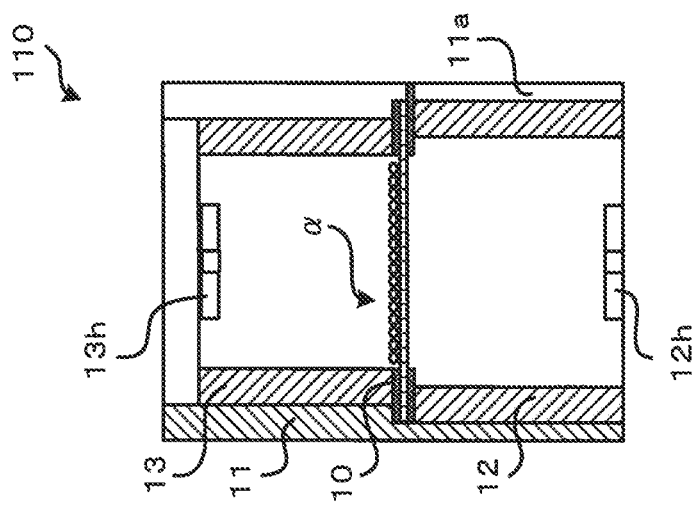

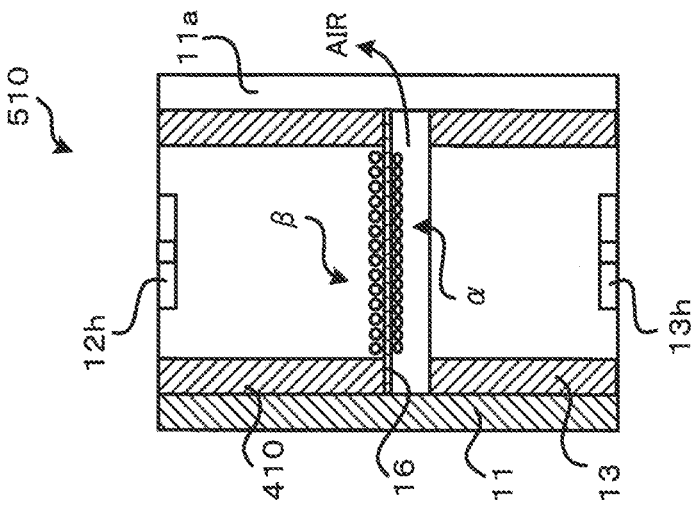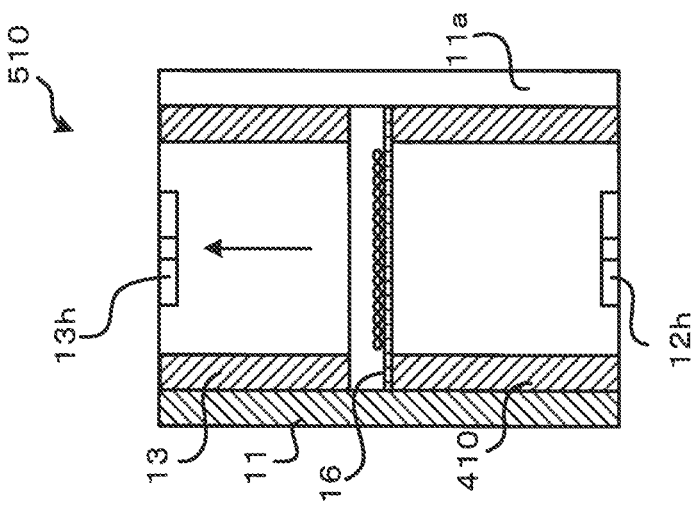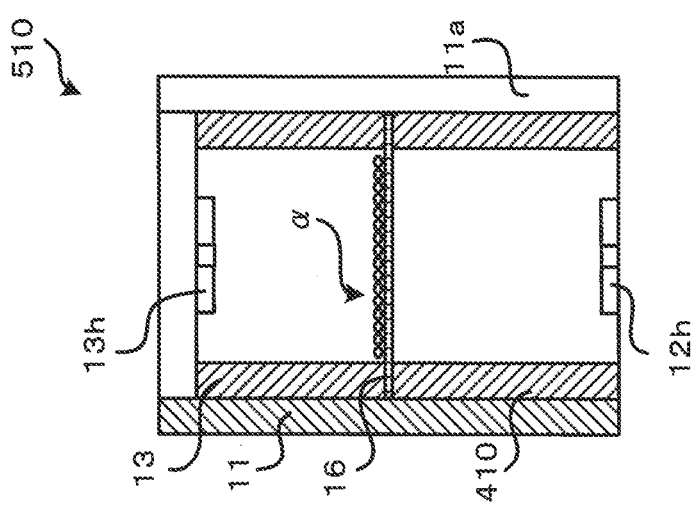

Fig.14

| SAMPLE NO. | CONFIGURATION ||||| CONDITIONS OF FIXATION ||| EVALUATION ||
|---|---|---|---|---|---|---|---|---|---|---|
| | PU MEMBRANE | PU/SUBSTRATE | SUBSTRATE/PU/BASE PLATE | MELTED SUBSTRATE/PU/BASE PLATE | | LOAD (g) | CURRENT (mA) | TIME (seconds) | PEELING TEST | OBSERVATION OF SECTION |
| 1 | ONE-SIDED MEMBRANE | PU/PET | — | — | | 300 | 3 | 10 | ○ | ○ |
| 2 | ONE-SIDED MEMBRANE | PU/PET | — | — | | 500 | 3 | 5 | ○ | ○ |
| 3 | ONE-SIDED MEMBRANE | PU/PET | — | — | | 900 | 2 | 5 | ○ | ○ |
| 4 | ONE-SIDED MEMBRANE | PU/PET | — | — | | 450 | 2 | 5 | × | × |
| 5 | FLAT MEMBRANE | PU/PET | — | — | | 500 | 3 | 10 | × | — |
| 6 | ONE-SIDED MEMBRANE | PU/PP | — | — | | 200 | 2 | 3 | ○ | ○ |
| 7 | TWO-SIDED MEMBRANE | — | PP/PU/PP | — | | | 3 | 10 | ○ | ○ |
| 8 | TWO-SIDED MEMBRANE | — | — | PP(235°C)/PU/PP | | MELT SUBSTRATE AT 235°C ||| ○ | — |

CELL CULTURE DEVICE AND METHOD OF MANUFACTURING THE SAME

CROSS-REFERENCE TO RELATED APPLICATION

The present application claims priority from Japanese patent application P2015-154078 filed on Aug. 4, 2015, the content of which is hereby incorporated by reference into this application.

BACKGROUND

Technical Field

The present disclosure relates to a cell culture device and a method of manufacturing the same.

Description of the Related Art

The cell culture technology has recently been drawn attention as the useful technique in various fields such as drug development and regenerative medicine. A method using a membrane scaffold (cell culture membrane) has been known as an example of the method of culturing a scaffold-based cells. A cell culture device in which the cell culture membrane is fixed to a substrate has generally been used for cell culture using such a cell culture membrane, for the purpose of, for example, reinforcing the cell culture membrane and facilitating handling of the cell culture membrane.

An available technique of fixing the cell culture membrane to the substrate is a method using, for example, an adhesive tape or an adhesive agent. In this method, however, an additive included in the adhesive tape or the adhesive agent is likely to be eluted in a culture solution and affect cell culture. A method proposed to fix the cell culture membrane to the substrate while suppressing elution of an additive that is likely to affect cell culture, into a culture solution is a method that makes both the cell culture membrane and the substrate from thermoplastic resins and welds the cell culture membrane and the substrate to each other by heat or ultrasonic vibration (for example, JP 2011-120504A).

When the cell culture membrane and tile substrate are fixed to each other by welding, however, the cell culture membrane is swollen together with the substrate by heating in the welding process. When the temperature is subsequently decreased to complete the welding, the cell culture membrane is contracted together with the substrate. This is likely to cause deformation of the cell culture membrane in the neighborhood of the welded part (for example, stretch or wrinkle) and damage the flatness on a culture surface of the cell culture membrane. In the cell culture membrane, reducing the flatness on the culture surface is likely to affect cultured cells and provide noise of the culture condition during cell culture. This is likely to fail to keep the culture conditions sufficiently constant and thereby cause a problem, such as variability in results of analysis.

SUMMARY

At least part of the problems described above may be solved by any of various aspects described below.

(1) According to one aspect, there is provided a cell culture device comprising a cell culture membrane and a substrate fixed to the cell culture membrane. In the cell culture device of this aspect, the cell culture membrane is made from a thermosetting resin and has a plurality of pores that are open to at least one surface including a surface on a side that is in contact with the substrate. The substrate is made from a thermoplastic resin. In a contact region between the cell culture membrane and the substrate, part of the substrate is extended to form bulges in the pores of the cell culture membrane that are open in the contact region.

The configuration of the cell culture device of this aspect enhances the strength of fixation between the cell culture membrane and the substrate, and suppresses elution of a substance that is likely to affect cultured cells, into a culture solution during cell culture using the cell culture device. Unlike the configuration that both a cell culture membrane and a substrate are made from thermoplastic resins and are welded to each other, this configuration keeps the shape of the cell culture membrane and thereby suppresses reduction of the strength of the cell culture membrane caused by the fixation process of the cell culture membrane to the substrate. Additionally the cell culture membrane is made from the thermosetting resin. This suppresses deformation of the cell culture membrane when the cell culture membrane is fixed to the substrate. This maintains the membrane accuracy of the cell culture membrane (flatness of the membrane) and reduces variability of the cell culture conditions due to the reduction of the membrane accuracy.

(2) In the cell culture device of the above aspect, the thermosetting resin from which the cell culture membrane is made may be polyurethane. The cell culture device of this aspect readily provides the cell culture membrane that is a flexible porous membrane suitable for cell culture.

(3) In the cell culture device of the above aspect, the thermoplastic resin from which the substrate is made may be a resin selected from the group consisting of polyethylene, polypropylene, polystyrene, AS resin, ABS resin, polyvinyl chloride, acrylic resin, polyethylene terephthalate, polybutylene terephthalate, polyvinyl alcohol, polyvinylidene fluoride, nylon 6, nylon 66, nylon 12, polyacetal, polycarbonate, polyether imide, polysulfone, polychlorotrifluoroethylene and polylactic acid. The configuration of the cell culture device of this aspect suppresses elution of a substance that is likely to affect cultured cells, into a culture solution during cell culture.

(4) In the cell culture device of the above aspect, the cell culture membrane may have a thickness of 0.1 to 100 µm. In the cell culture device of this aspect, the cell culture membrane is a flexible porous membrane suitable for cell culture.

(5) In the cell culture device of the above aspect, the cell culture membrane may have an average pore diameter of 0.1 to 100 µm in the surface on the side that is in contact with the substrate. In the cell culture device of this aspect, the cell culture membrane is a flexible porous membrane suitable for cell culture.

(6) In the cell culture device of the above aspect, the substrate may be a ring-shaped sheet that has a thickness of 0.05 to 0.5 mm and includes a ring-shaped frame body. The cell culture membrane may be fixed to the frame body of the substrate such as to close an opening of the ring-shaped sheet. The configuration of the cell culture device of this aspect facilitates reinforcement of the cell culture membrane by the substrate and allows cultured cells on the cell culture membrane to be observed without detachment of the substrate from the cell culture membrane after cell culture using the cell culture device.

(7) The cell culture device of the above aspect may further comprise a base that is configured to hold the substrate. The substrate and the base may be assembled by engagement. After cell culture using the cell culture device, the configuration of the cell culture device of this aspect enables the substrate to be readily detached from the base. This simplifies the operation for observing cultured cells on the cell culture membrane.

(8) In the cell culture device of the above aspect, at least part of the plurality of pores included in the cell culture membrane may be through holes formed to pass through the cell culture membrane in a membrane thickness direction. The substrate may be made from the thermoplastic resin and may comprise a first substrate portion placed on a first surface of the cell culture membrane and a second substrate portion placed on a second surface of the cell culture membrane. The contact region may include a first contact region in which the first substrate portion comes into contact with the first surface of the cell culture membrane and a second contact region in which the second substrate portion comes into contact with the second surface of the cell culture membrane. In both the first contact region and the second contact region, part of the first substrate portion and part of the second substrate portion may be extended to form bulges in the pores of the cell culture membrane that are open in either of the first and the second contact regions. The configuration of the cell culture device of this aspect causes the cell culture membrane having the through holes formed as the pores to be reinforced by the pair of substrate portions, and enhances the strength of fixation between the cell culture membrane and the pair of substrate portions.

(9) In the cell culture device of the above aspect, at least part of the plurality of pores included in the cell culture membrane may be through holes formed to pass through the cell culture membrane in a membrane thickness direction. The substrate may be made from the thermoplastic resin and may comprise a first substrate portion placed on a first surface of the cell culture membrane and a second substrate portion placed on a second surface of the cell culture membrane. The contact region may include a first contact region in which the first substrate portion comes into contact with the first surface of the cell culture membrane and a second contact region in which the second substrate portion comes into contact with the second surface of the cell culture membrane. The first substrate portion and the second substrate portion may be connected with each other by bulges that are extended from at least one of the first substrate portion and the second substrate portion via the through holes formed in the cell culture membrane to be open in the first and the second contact regions. The configuration of the cell culture device of this aspect causes the cell culture membrane having the through holes formed as the pores to be reinforced by the pair of substrate portions, and enhances the strength of fixation between the cell culture membrane and the pair of substrate portions.

(10) According to another aspect, there is provided a method of manufacturing a cell culture device comprising a cell culture membrane and a substrate fixed to the cell culture membrane. The method of manufacturing the cell culture device comprises: providing a porous membrane that is made from a thermosetting resin and has a plurality of pores that are open to at least one surface, as the cell culture membrane; providing a substrate that is made from a thermoplastic resin, as the substrate; melting or softening the thermoplastic resin from which the substrate is made, by temperature rising of a surface portion of the substrate in an area including a fixation area to be fixed to the cell culture membrane; and simultaneously with or after the melting or softening the thermoplastic resin, stacking and pressing the cell culture membrane and the substrate on each other and against each other, such that the surface of the cell culture membrane to which the plurality of pores are open comes into contact with a melted or softened portion of the substrate, and forming bulges in the pores of the cell culture membrane by extending part of the melted or softened thermoplastic resin from which the substrate is made.

The configuration of the method of manufacturing the cell culture device of this aspect enhances the strength of fixation between the cell culture membrane and the substrate, and suppresses elution of a substance that is likely to affect cultured cells, into a culture solution during cell culture using the manufactured cell culture device. Unlike the method that makes both a cell culture membrane and a substrate from thermoplastic resins and welds the cell culture membrane and the substrate to each other, this configuration keeps the shape of the cell culture membrane and thereby suppresses reduction of the strength of the cell culture membrane caused by the fixation process of the cell culture membrane to the substrate. Additionally, the cell culture membrane is made from the thermosetting resin. This suppresses deformation of the cell culture membrane when the cell culture membrane is fixed to the substrate. This maintains the membrane accuracy of the cell culture membrane (flatness of the membrane) and reduces variability of the cell culture conditions due to the reduction of the membrane accuracy.

There are various aspects other than those described above, for example, a method of holding the cell culture membrane or a cell culture method using the cell culture device.

The configuration of the cell culture device of any of the above aspects enhances the strength of fixation between the cell culture membrane and the substrate, and suppresses elution of a substance that is likely to affect cultured cells, into a culture solution during cell culture using the cell culture device. Unlike the configuration that both a cell culture membrane and a substrate are made from thermoplastic resins and are welded to each other, this configuration keeps the shape of the cell culture membrane and thereby suppresses reduction of the strength of the cell culture membrane caused by the fixation process of the cell culture membrane to the substrate. Additionally, the cell culture membrane is made from the thermosetting resin. This suppresses deformation of the cell culture membrane when the cell culture membrane is fixed to the substrate. This maintains the membrane accuracy of the cell culture membrane (flatness of the membrane) and reduces variability of the cell culture conditions due to the reduction of the membrane accuracy.

BRIEF DESCRIPTION OF THE DRAWINGS

FIG. 4 is a process chart showing a method of manufacturing the cell culture device;

FIGS. 9A to 9C are sectional diagrams illustrating two-sided culture using the cell culture device of the third embodiment;

FIGS. 12A to 12C are sectional diagrams illustrating application of a cell culture device according to a modification of the fourth embodiment;

FIG. 14 is a table showing results of a fixation test;

DESCRIPTION OF THE EMBODIMENTS

A. First Embodiment

A-1. General Configuration of Cell Culture Device

Figure 1:
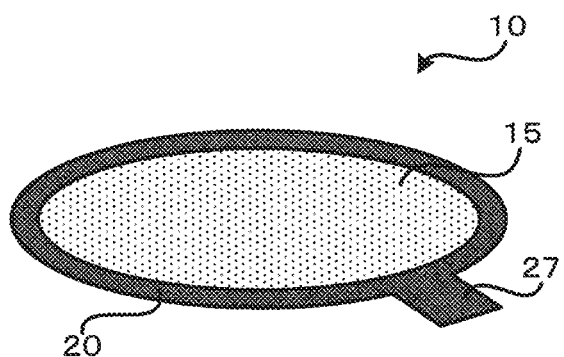
FIG. 1 is a perspective view schematically illustrating the configuration of a cell culture device according to a first embodiment.
Figure 2:
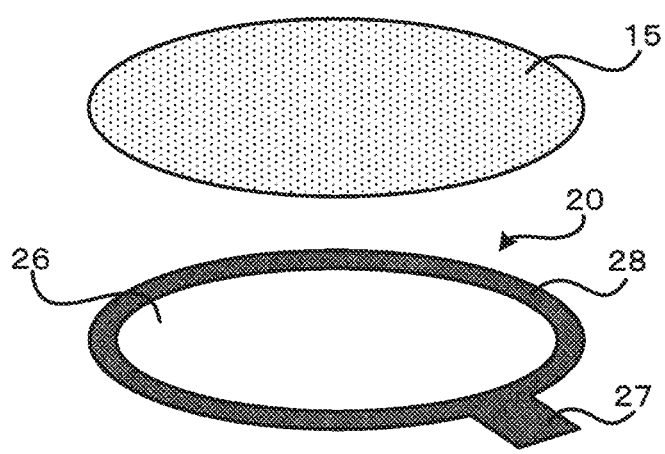
FIG. 2 is an exploded perspective view illustrating assembly of the cell culture device.

FIG. 1 is a perspective view schematically illustrating the configuration of a cell culture device 10 according to a first embodiment. FIG. 2 is an exploded perspective view illustrating assembly of the cell culture device 10. The cell culture device 10 includes a cell culture membrane 15 and a substrate 20.

The cell culture membrane 15 is a porous membrane in an approximately circular shape. As shown in FIG. 2, the substrate 20 is formed from a ring-shaped sheet having a circular hole 26 at the center. The hole 26 of the substrate 20 is formed to have a smaller outer diameter than the outer diameter of the cell culture membrane 15. The substrate 20 is formed to have an outer diameter that is approximately equal to the outer diameter of the cell culture membrane 15. In the cell culture device 10 of the embodiment, the cell culture membrane 15 is placed on the substrate 20 to close the hole 26, and the cell culture membrane 15 and the substrate 20 are fixed to each other. In the description hereof, the configuration that "the substrate 20 and the cell culture membrane 15 are fixed to each other" means the configuration that the substrate 20 and the cell culture membrane 15 are joined together to keep the integrity without changing the positional relationship between the substrate 20 and the cell culture membrane 15 in a series of operations for cell culture using the cell culture device 10. This embodiment is characterized by the configuration of fixation between the substrate 20 and the cell culture membrane 15.

A-2. Configuration of Cell Culture Membrane

The cell culture membrane 15 is a membrane serving as a scaffold of cultured cells during cell culture and is made from a thermosetting resin according to this embodiment. The thermosetting resin from which the cell culture membrane 15 is made may be a resin selected from the group consisting of, for example, polyurethane, polyurea, silicone resin, phenolic resin, epoxy resin, unsaturated polyester and polyimide.

Figure 3A:
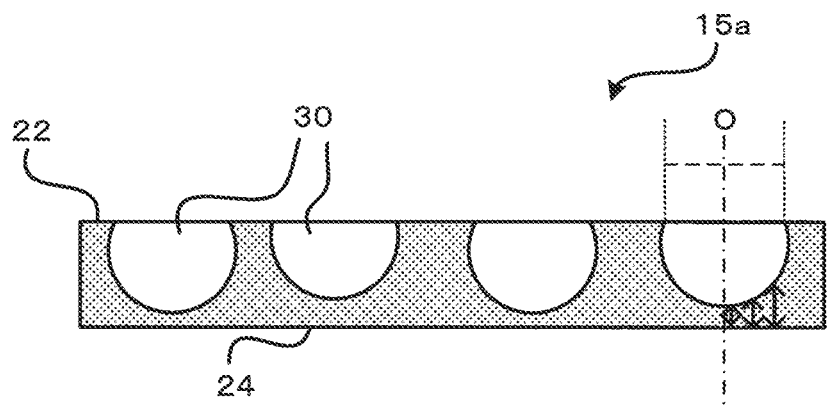
FIGS. 3A to 3C are schematic sectional views illustrating the schematic configurations of cell culture membranes.
Figure 3B:
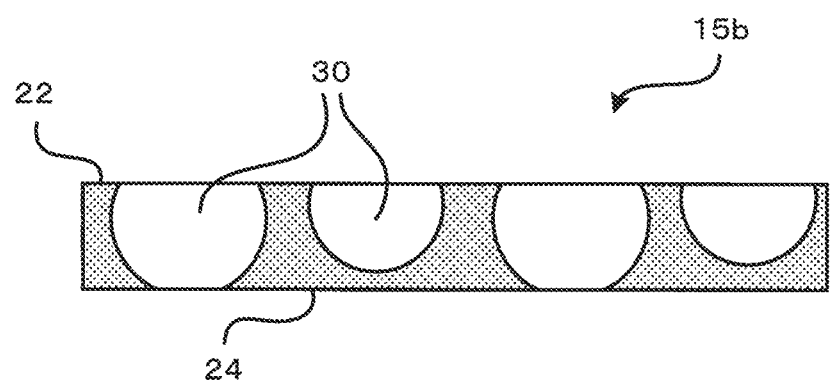
Figure 3C:
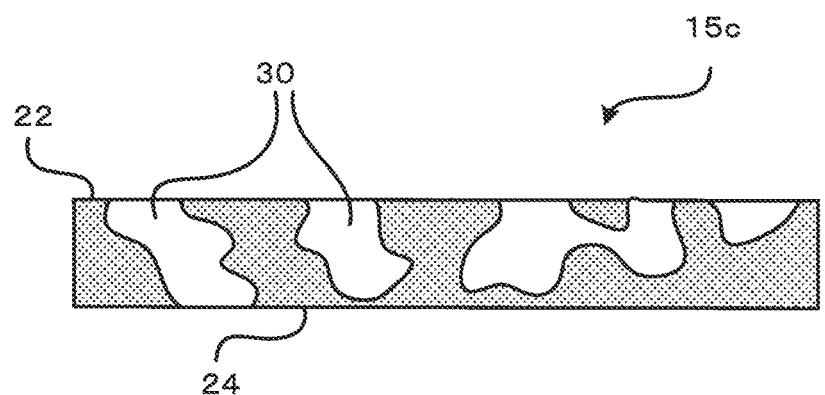

FIGS. 3A to 3C are sectional views illustrating the schematic configurations of cell culture membranes 15a to 15c.

The cell culture membrane 15 is a porous membrane having a plurality of pores 30 that are open to at least one surface. In other words, the cell culture membrane 15 has a plurality of concaves and convexes formed in at least one surface. The cell culture membrane 15 has a surface 22 as a first face and a rear face 24 as a second face. The plurality of pores 30 described above are all open to at least the surface 22. The average pore diameter of the pores 30 on the surface 22 may be, for example, 0.1 to 100 μm. The average pore diameter of the pores 30 of the cell culture membrane 15 is a value determined by observing the surface of the cell culture membrane 15 with a scanning electron microscope (SEM). More specifically, a concrete procedure may measure the maximum lengths of all the pores observed in a specified field of view in an SEM image of the surface of the cell culture membrane 15 at 1000-fold magnification and calculate the average of the measured values. The maximum length herein denotes a maximum value among the lengths of the respective sides of a rectangle circumscribing each pore. The average pore diameter in the above range readily provides both the flexibility and the strength of the cell culture membrane 15. The average pore diameter on the surface 22 of the cell culture membrane 15 may, however, be less than 0.1 μm or may be greater than 100 μm.

The cell culture membrane 15 may have the thickness of, for example, 0.1 to 100 μm. The thickness of the cell culture membrane 15 denotes a distance from the rear face 24 to the highest position of the convex among the concaves and the convexes formed on the surface 22 of the cell culture membrane 15. The membrane thickness in the above range readily provides both the flexibility and the strength of the cell culture membrane 15. The thickness of the cell culture membrane 15 may, however, be less than 0.1 μm or may be greater than 100 μm.

The plurality of pores 30 may be open to only the surface 22, or at least part of the plurality of pores 30 may be provided as through holes open to both the surface 22 and the rear face 24. In a cell culture membrane 15a shown in FIG. 3A, all pores 30 are open to only the surface 22. In a cell culture membrane 15b shown in FIG. 3B and in a cell culture membrane 15c shown in FIG. 3C, part of pores 30 are provided as through holes that are open to both the surface 22 and the rear face 24. The cell culture membrane 15 of this embodiment is fixed to the substrate 20 at the surface 22 to which the pores 30 are open.

The cell culture membrane 15 used may be, for example, a membrane having single pores 30 in a membrane thickness direction as shown in FIG. 3A or FIG. 3B. These pores 30 may be formed to have inner wall of substantially curved surface as a whole as shown in FIG. 3A or in FIG. 3B. In another example, the pore 30 may be formed in irregular shapes as shown in FIG. 3C. A membrane with pores 30 formed in various shapes may be used for the cell culture membrane 15. A porous membrane with single pores 30 provided in the membrane thickness direction is advantageous as the cell culture membrane.

When a porous membrane having a large number of pores that are formed to pass through the membrane in the thickness direction is used as the cell culture membrane 15, different types of cells may be cultured on the respective surfaces for the purpose of analysis of interactions between the different types of cells as described later. It is thus especially desirable to form the cell culture membrane 15 from polyurethane in terms of, for example, ease of forming through holes that pass through the membrane in the thickness direction (for example, through holes formed by single pores to pass through the membrane in the thickness direction), high elasticity and high strength and resulting ease of providing a flexible porous membrane suitable for cell culture.

A porous polyurethane membrane used as the cell culture membrane 15 may be manufactured by, for example, the following process. The process first provides an uncured polyurethane raw material including a polyol such as polyether polyol, an isocyanate such as an aromatic isocyanate, and a diluting agent. The process subsequently forms a layer of the provided uncured polyurethane raw material on a base plate for membrane formation. The process then cures the layer of the polyurethane raw material with supplying water vapor to the layer of the uncured polyurethane raw material, so as to obtain a polyurethane porous membrane.

More specifically, when water vapor is supplied through an exposed surface side of the layer of the uncured polyurethane raw material, a reaction proceeds between the isocyanate in the polyurethane raw material and the water vapor to produce carbon dioxide. As a result, polyurethane in the middle of curing is foamed (to form pores inside) to be porous. The water vapor serves as a foaming agent of polyurethane. Supplying the water vapor serving as the foaming agent through the exposed surface side causes pore formation to proceed from the exposed surface side. In the polyurethane porous membrane, pores open to the exposed surface side (surface 22-side) are thus generally formed as shown in FIGS. 3A to 3C.

A concrete method of supplying the water vapor to the layer of the uncured polyurethane raw material may place the layer of the uncured polyurethane raw material on the base plate for membrane formation, for example, in a closed container containing water, such that the exposed surface of the layer of the uncured polyurethane raw material is exposed to water. The inside of the closed container is maintained at a predetermined temperature to be kept at a saturated vapor pressure. The water vapor is accordingly supplied through the surface of the layer of the uncured polyurethane raw material, and a reaction proceeds between the isocyanate in the polyurethane raw material and the water vapor to produce carbon dioxide. In the meantime, a curing reaction proceeds between the polyol and the isocyanate.

The shape of the polyurethane porous membrane may be controlled by adjusting conditions selected among the reaction temperature and the reaction time in the curing reaction with supply of the water vapor described above, the amount of water vapor supplied during curing and the composition of the polyurethane raw material. Adjusting these conditions provides the pores 30 in the shape shown in FIG. 3A and FIG. 3B. More specifically when the bottom face of the pore 30 that is the inner wall surface of the pore 30 closer to the rear face 24 than the surface 22 is viewed in a cross section of the cell culture membrane 15 perpendicular to the membrane thickness direction, the pore 30 may be formed such that the distance of the bottom face of the pore 30 from the rear face 24 gradually decreases with a decrease in distance from the center of the bottom face of the pore 30. In FIG. 3A, a center axis O denotes the center axis of the pore 30 in the cross section of the cell culture membrane 15a perpendicular to the membrane thickness direction. Arrows indicate the state that the distance between the bottom face of the pore 30 and the rear face 24 decreases with a decrease in distance from the center axis O.

The porous membrane made from the thermosetting resin and used as the cell culture membrane 15 may appropriately be subjected to a treatment for enhancing the affinity to the cells (for example, treatment of making the surface of the substrate hydrophilic), prior to the use. The polyurethane porous membrane is, however, generally usable as the scaffold of cultured cells without such surface treatment.

A-3. Configuration of Substrate

The substrate 20 is a member fixed to the cell culture membrane 15 to reinforce the cell culture membrane 15 and is provided as a ring-shaped sheet having a circular hole 26 at the center. As shown in FIG. 2, the substrate 30 includes a ring-shaped frame body 28 and a projection 27 that is protruded outward in the radial direction from a specified position on the outer circumference of the frame body 28. The projection 27 is a structure clamped with tweezers or the like to hold the substrate 20. This configuration enables the cell culture device 10 to be readily handled without touching the cell culture membrane 15 and cultured cells. According to a modification, the substrate 20 may not have the projection 27 described above.

The substrate 20 may have thickness of, for example, 0.05 to 0.5 mm. This configuration facilitates reinforcement of the cell culture membrane 15 by the substrate 20 and also enables cultured cells on the cell culture membrane 15 to be observed without detaching the cell culture membrane 15 from the substrate 20 after cell culture on the cell culture membrane 15 using the cell culture device 10. Accordingly this configuration does not cause the substrate 20 to interfere with microscopic observation or the like and enables the cell culture membrane 15 to be readily handled for observation. The thickness of the substrate 20 may, however, be less than 0.05 mm or may be greater than 0.5 mm.

According to this embodiment, the substrate 20 is made from a thermoplastic resin. The substrate 20 is generally soaked together with the cell culture membrane 15 in a culture solution in the process of cell culture using the cell culture membrane 15. The thermoplastic resin from which the substrate 20 is made may thus be a resin from which only an allowable level of sufficiently small amount of a substance that is likely to affect cultured cells is eluted in the culture solution during cell culture. The substrate 20 may also be made from a material having a specific gravity that does not cause the cell culture device 10 to float in the culture solution when the cell culture device 10 is soaked in the culture solution for the purpose of cell culture. From these standpoints, the thermoplastic resin from which the substrate 20 is made may be a resin selected from the group consisting of, for example, polyethylene, polypropylene, polystyrene, AS resin, ABS resin, polyvinyl chloride, acrylic resin, polyethylene terephthalate, polybutylene terephthalate, polyvinyl alcohol, polyvinylidene fluoride, nylon 6, nylon 66, nylon 12, polyacetal, polycarbonate, polyether imide, polysulfone, polychlorotrifluoroethylene and polylactic acid.

According to this embodiment, as described later, in order to fix the substrate 20 to the cell culture membrane 15, the surface of the substrate 20 is melted or softened by temperature rising, and the cell culture membrane 15 and the substrate 20 are stacked and pressed against each other, so that the melted or softened thermoplastic resin from which the substrate 20 is made is extended into the pores 30 of the cell culture membrane 15. The thermoplastic resin from which the substrate 20 is made may be melted and softened in a temperature range that is lower than the decomposition temperature of the thermosetting resin from which the cell culture membrane 15 is made and suppresses decomposition and degradation of the cell culture membrane 15, so as to be extended into the pores 30 by pressing.

From this standpoint, the thermoplastic resin from which the substrate 20 is made may be, for example, a resin having a melt flow rate (hereinafter abbreviated as MFR) measured under a temperature condition of glass transition temperature +50° C. or an MFR measured under a temperature condition of melting point +50° C. according to the definition of JIS K7210 that is not lower than 0.01 g/10 minutes under 2.16 kg load. The value of MFR smaller than the above range indicates that the thermoplastic resin has a large molecular weight and provides low flowability by temperature rising. This may make it difficult to extend the thermoplastic resin from which the substrate 20 is made, into the pores 30. The glass transition temperature or the melting point of the thermoplastic resin described above denotes a temperature determined according to the definitions described in JIS K7121 "Method of measuring transition temperature of plastic".

The thermoplastic resin from which the substrate 20 is made may be a thermoplastic resin having a softening point of not higher than 250° C. In the case of a thermoplastic resin having the softening point of higher than this temperature range, the temperature of the substrate 20 is required to be raised to a rather high temperature, in order to provide the flowability that allows the thermoplastic resin to be extended into the pores 30. This may result in deteriorating the thermoplastic resin from which the cell culture membrane 15 is made. The softening point described above denotes a temperature determined according to the definition of Vicat softening point described in JIS K7206.

When, for example, polypropylene (PP) is used as the thermoplastic resin to form the substrate 20, the average molecular weight of polypropylene is desirably in a range of 10,000 to 500,000. The larger average molecular weight than this range may provide the melted or softened resin with the insufficient flowability and may make it difficult to extend the melted or softened resin into the pores 30. The smaller average molecular weight than the above range may, on the other hand, make it difficult to keep the shape after formation of the substrate 20.

A-4. Method of Manufacturing Cell Culture Device

FIG. 4 is a process chart showing a method of manufacturing the cell culture device 10. In the process of manufacturing the cell culture device 10, the cell culture membrane 15 and the substrate 20 described above are provided first (step S100). The cell culture membrane 15 is subsequently placed on the substrate 20 (step S110). When the pores 30 of the cell culture membrane 15 are open to only one surface, the substrate 20 is brought into contact with the surface to which the pores 30 are open. When at least part of the pores 30 of the cell culture membrane 15 are formed as through holes, it is desirable to bring the substrate 20 into contact with a surface having a higher rate of the pores open to the surface.

While the temperature of the substrate 20 is raised to a temperature that melts or softens the substrate 20, the substrate 20 and the cell culture membrane 15 are pressed against each other in the stacking direction to be fixed to each other (step S120). This completes the cell culture device 10. At step S120, the temperature of the substrate 20 is raised to the temperature that melts or softens the surface of the substrate 20 that is in contact with the cell culture membrane 15, so that the melted or softened thermoplastic resin is extended into the pores 30 of the substrate 20 by pressing. As a result, after the temperature of the substrate 20 is decreased, bulges are formed from the extended thermoplastic resin in the pores 30, so as to fix the substrate 20 to the cell culture membrane 15.

Figure 5A:
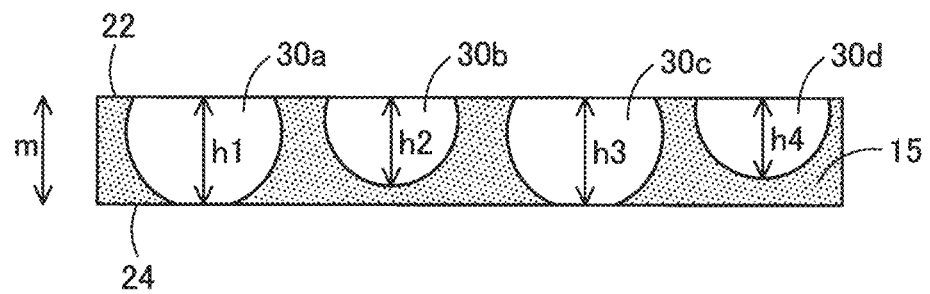
FIGS. 5A and 5B are diagrams illustrating bulges formed in pores.
Figure 5B:
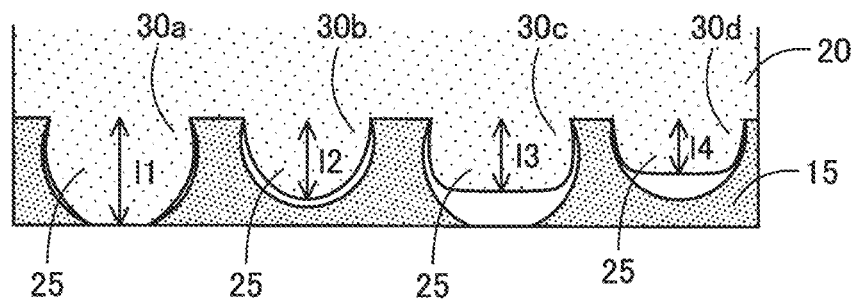

FIGS. 5A and 5B are diagrams illustrating bulges 25 formed in the pores 30. FIG. 5A is a diagram schematically illustrating a section of the cell culture membrane 15. FIG. 5B is a schematic sectional view illustrating the state after fixation of the substrate 20 to the cell culture membrane 15. The cell culture membrane 15 shown in FIGS. 5A and 5B is a porous membrane having part of the pores 30 formed as through holes. FIG. 5A illustrates four pores 30a to 30d. In FIG. 5A, the depths of the respective pores 30a to 30d are shown by h1 to h4. The depth of each pore 30 denotes a distance from a virtual surface to the deepest position of the pore 30 (i.e., the position of the wall surface of the pore most distant from the virtual surface in the membrane thickness direction). The virtual surface herein denotes a plane that is parallel to the rear face 24 of the cell culture membrane 15 in contact with the base plate for membrane formation and that goes through the highest position of the convex among the concaves and convexes formed on the surface 22. With regard to the pores 30a and 30c formed as through holes, the depth of the pore is equal to a membrane thickness m of the cell culture membrane 15.

FIG. 5B illustrates formation of the bulges 25 in the respective pores 30a to 30b by extending part of the substrate 20 into the respective pores 30a to 30d. In FIG. 5B, the penetration depths of the respective bulges 25 are shown by l1 to l4. The penetration depth of each bulge 25 denotes a distance from the virtual surface described above to the most protruded position of the bulge 25 (i.e., the position of the surface of the bulge most distant from the virtual surface in the membrane thickness direction). The bulge 25 formed in the pore 30a shown in FIG. 5B has the penetration depth l1 that is equal to the membrane thickness m.

In the cell culture device 10 of the embodiment, the state that "bulges 25 are formed in the pores 30 of the cell culture membrane 15" indicates the following. A section of the joint region between the cell culture membrane 15 and the substrate 20 is observed at 1000-fold magnification with a scanning electron microscope (SEM). The depths of the respective pores 30 are measured in an arbitrarily selected field of view, and the depth of the deepest pore 30 (maximum depth) is specified. In the case of the cell culture membrane 15 having through holes, the maximum depth is equal to the membrane thickness m. The penetration depths of the bulges 25 formed in the respective pores 30 are also measured. The state that the rate of the pores 30 with the bulges 25 having the penetration depths of not lower than 30% of the above maximum depth is not lower than 30% of the total number of the pores 30 in the field of view is expressed as the state that "bulges 25 are formed in the pores 30 of the cell culture membrane 15".

The rate of the pores 30 with the bulges 25 having the penetration depths of not lower than 30% of the above maximum depth is desirably not lower than 50% of the total number of the pores 30 in the field of view and is more desirably not lower than 80% of the total number of the pores in the field of view. The rate of the pores 30 with the bulges 25 having the penetration depths of not lower than 50% of the above maximum depth is desirably not lower than 30% of the total number of the pores in the field of view, is more desirably not lower than 50% and is furthermore desirably not lower than 80%. The rate of the pores 30 with the bulges 25 having the penetration depths of not lower than 80% of the above maximum depth is desirably not lower than 30% of the total number of the pores in the field of view, is more desirably not lower than 50% and is furthermore desirably not lower than 80%. This enhances the strength of fixation between the cell culture membrane 15 and the substrate 20.

A process employed to raise the temperature of the substrate 20 at step S120 may be any process that melts or softens the surface of the substrate 20 in an area including an area that is to be fixed to the cell culture membrane 15, in order to form the bulges 25. The temperature rising process may be heating with a heater or a heat plate, by infrared radiation or the like or may be heating with ultrasonic wave. The temperature of the temperature rising and the pressure applied for pressing at step S120 may be set arbitrarily to form the bulges 25 in the pores 30 as described above by taking into account (i), (ii) described below, and the like. (i) is the degree of an increase in flowability of the thermoplastic resin from which the substrate 20 is made by temperature rising. (ii) is the heatproof temperature of the thermosetting resin from which the cell culture membrane 15 is made. The pressure applied for pressing may be a pressure that does not substantially damage the structure of the cell culture membrane 15 including the pores 30 by pressing.

In FIG. 4, step S100 corresponds to the "first process" and the "second process" described in SUMMARY, and step S120 corresponds to the "third process" and the "fourth process" described in SUMMARY.

The cell culture device 10 manufactured as described above may be placed in, for example, a well of a plate for cell culture, and the well may be filled with a culture solution. Desired cells are then seeded on a surface the cell culture membrane 15. The surface on which cells are seeded may be the surface to which the pores 30 are open (surface 22). The frame body 28 or the projection 27 of the substrate 20 may be held to handle the cell culture device 10. After cell culture, the cell culture membrane 15 may be subjected to microscopic observation (for example, observation with a confocal laser microscope) without being detached from the substrate 20.

The cell culture device 10 of the embodiment having the configuration described above or the method of manufacturing the cell culture device 10 forms the bulges 25 by extending part of the substrate 20 inside of the pores 30 of the cell culture membrane 15 that are open in the contact region between the cell culture membrane 15 and the substrate 20. This enhances the strength of fixation of the cell culture membrane 15 and the substrate 20 to each other. There is no need to use an adhesive or the like for fixation. This accordingly suppresses a substance that is likely to affect cultured cells from being eluted in a culture solution during cell culture using the cell culture device 10.

Unlike fixation of the cell culture membrane and the substrate to each other by welding or the like, the configuration of this embodiment suppresses reduction of the strength of the cell culture membrane 15 and maintains the membrane accuracy (flatness of the membrane). The method employed to fix the cell culture membrane and the substrate to each other may be a method that forms the cell culture membrane from a thermosetting resin, forms the substrate from a thermoplastic resin and provides bulges in pores of the cell culture membrane like the embodiment described above or may be a method that forms both the cell culture membrane and the substrate from thermoplastic resins and thermally welds the cell culture membrane and the substrate to each other. In the method of forming both the cell culture membrane and the substrate from thermoplastic resins and thermally welding the cell culture membrane and the substrate to each other, however, the cell culture membrane, in addition to the substrate, is melted during welding. Applying a pressing force in the state that both the substrate and the cell culture membrane are melted flattens and thins the cell culture membrane in a welded portion. This is likely to cause a problem, such as reducing the strength of the membrane and reducing the durability of the entire cell culture device. Expanding and contracting the cell culture membrane accompanied with temperature rising and temperature decreasing in the course of welding is likely to cause deformation (for example, stretch or wrinkle) of the cell culture membrane in the neighborhood of the welded region and reduce the flatness on the culture surface of the cell culture membrane. In the cell culture membrane, reducing the flatness on the culture surface is likely to affect cultured cells and provide noise of the culture condition. This is likely to cause a problem, such as variability in results of analysis. The cell culture device 10 of the embodiment is, however, manufactured by making the cell culture membrane 15 from a thermosetting resin and melting or softening only the substrate 20 formed from a thermoplastic resin to be fixed to the cell culture membrane 15. This maintains the shape of the cell culture membrane 15 even in the fixation region and thereby suppresses reduction of the strength of the membrane. This also suppresses expansion and contraction of the cell culture membrane in the course of fixation, thus suppressing undesired deformation of the cell culture membrane 15 and maintaining the membrane accuracy (flatness of the membrane).

As described above, when the cell culture membrane 15 is formed from polyurethane, the inner wall of the pore 30 can be formed in the approximately curved shape as a whole as shown in FIG. 3A, FIG. 3B, FIG. 5A and FIG. 5B by adjusting the condition for curing and making porous in the course of membrane formation. This configuration enables the thermoplastic resin from which the substrate 20 is made to be readily extended into the pores 30 and thereby facilitates formation of the bulges 25. Adjusting the above condition may form the pores 30 such that the diameter at the opening of the pore 30 is made smaller than the diameter at the deeper position of the pore 30 with regard to the diameters of the pore 30 in sections parallel to the surface 22. In the case of using the cell culture membrane 15 with the pores 30 having the narrowed opening, the anchor effect in the process of forming the bulges 25 in the pores 30 enhances the fixation force of the substrate 20 to the cell culture membrane 15.

B. Second Embodiment

Figure 6:
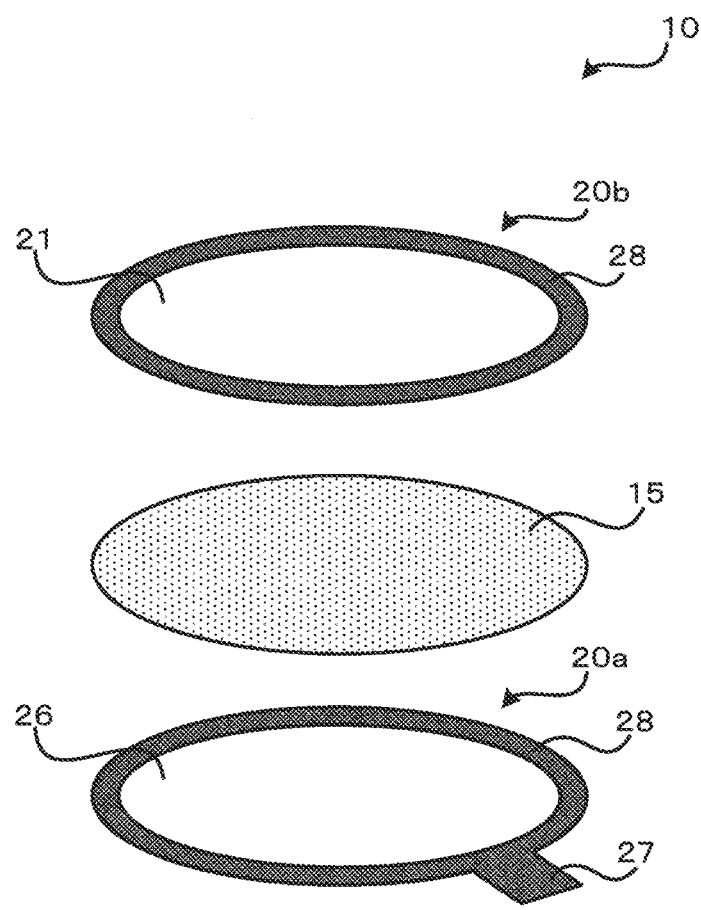
FIG. 6 is an exploded perspective view illustrating the configuration of a cell culture device according to a second embodiment.

FIG. 6 is an exploded perspective view illustrating the configuration of a cell culture device 10 according to a second embodiment. In the second embodiment, the like components to those of the first embodiment are expressed by the like reference numbers and are not described in detail. The cell culture device 10 of the second embodiment has the similar appearance to that of the cell culture device 10 of the first embodiment shown in FIG. 1 but differs from the cell culture device 10 of the first embodiment by providing substrate portions 20a and 20b as the substrate. More specifically, the cell culture device 10 of the second embodiment includes a substrate portion 20b that consists of a frame body 28 and is made from a thermoplastic resin, in addition to a substrate portion 20a that is the same as the substrate 20 in the cell culture device 10 shown in FIGS. 1 and 2, and the cell culture membrane 15 is placed between the pair of substrate portions 20a and 20b. When at least part of the pores 30 included in the cell culture membrane 15 are formed as through holes, placing the cell culture membrane 15 between the pair of substrate portions 20a and 20b enables bulges 25 to be extended and formed in the pores 30 with regard to each of the pair of substrate portions 20a and 20b. More specifically, in both a first contact region where the substrate portion 20a is in contact with a first surface of the cell culture membrane 15 (surface 22) and a second contact region where the substrate portion 20b is in contact with a second surface of the cell culture membrane 15 (rear face 24), bulges 25 may be formed by extending part of the respective substrate portions 20a and 20b into the pores 30 of the cell culture membrane 15 that are open to the contact region. Alternatively the substrate portions 20a and 20b may be connected with each other by means of bulges 25 extended from at least one of the substrate portions 20a and 20b through the pores 30 (through holes). This configuration provides the similar advantageous effects to those of the first embodiment.

The state that "in both the first contact region where the substrate portion 20a is in contact with the first surface of the cell culture membrane 15 and the second contact region where the substrate portion 20b is in contact with the second surface of the cell culture membrane 15, bulges 25 are formed by extending part of the respective substrate portions 20a and 20b into the pores 30 of the cell culture membrane 15 that are open to the contact region" (hereinafter called condition A) indicates the following. The conditions regarding the state that "bulges 25 are formed in the pores 30 of the cell culture membrane 15" described in the first embodiment are satisfied in each of the first contact region where the substrate portion 20a is in contact with the cell culture membrane 15 and the second contact region where the substrate portion 20b is in contact with the cell culture membrane 15.

The state that "the substrate portions 20a and 20b are connected with each other by means of bulges 25 extended from at least one of the substrate portions 20a and 20b through the pores 30 (through holes)" (hereinafter called condition B) indicates the following. Sections in contact regions between the cell culture membrane 15 and the respective substrate portions 20a and 20b are observed at 1000-fold magnification with a scanning electron microscope (SEM). With regard to all the pores 30 in an arbitrarily selected field of view, it is then determined whether the substrate portion 20a and the substrate portion 20b are connected with each other by means of bulges 25 extended from at least one of the substrate portions 20a and 20b. The state that the rate of the pores 30 in which the substrate portion 20a and the substrate portion 20b are connected with each other by means of bulges 25 is not lower than 30% of the total number of the pores 30 in the field of view is expressed as the state that "the substrate portions 20a and 20b are connected with each other by means of bulges 25 extended from at least one of the substrate portions 20a and 20b through the pores 30 (through holes)". It is desirable that the substrate portions 20a and 20b are connected with each other by means of bulges 25 in the pores 30 of not lower than 50% of the total number of the pores 30 in the field of view. It is more desirable that the substrate portions 20a and 20b are connected with each other by means of bulges 25 in the pores 30 of not lower than 80% of the total number of the pores 30 in the field of view.

Figure 7:
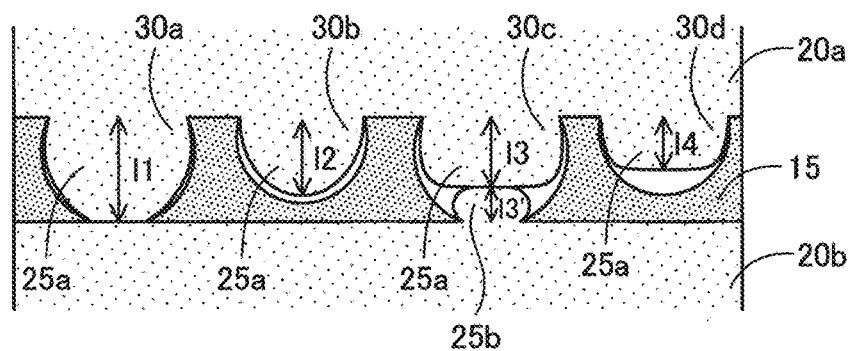
FIG. 7 is a diagram illustrating bulges formed in pores according to the second embodiment.

FIG. 7 is a diagram illustrating formation of bulges 25 in the pores 30 in the cell culture device 10 of the second embodiment, in a similar manner to FIGS. 5A and 5B. In FIG. 7, in a pore 30a provided as a through hole, a bulge 25a extended from the substrate portion 20a is in contact with the substrate portion 20b. In other words, a penetration depth I1 of the bulge 25a is equal to the membrane thickness. This state corresponds to the condition B described above. In FIG. 7, in a pore 30c provided as a through hole, a bulge 25a extended from the substrate portion 20a is in contact with a bulge 25b extended from the substrate portion 20b. In other words, the sum of a penetration depth I3 of the bulge 25a and a penetration depth I3' of the bulge 25b is equal to the membrane thickness. This state corresponds to both the condition A and the condition B described above. In the case where the bulge 25a and the bulge 25b are not in contact with each other in the pore 30c shown in FIG. 7, this state does not correspond to the condition B but corresponds to the condition A.

The configuration of the bulge 25 formed in the through hole may be changed according to a selected condition, for example, the type of the thermoplastic resin from which the substrate portions 20a and 20b are made, the configuration of the through holes including their diameters in the cell culture membrane 15 or the temperature in temperature rising at step S120. Satisfying either of the condition A and the condition B described above further enhances the strength of fixation between the cell culture membrane 15 and the substrate portions 20a and 20b.

In manufacture of the cell culture device 10 of the second embodiment, the process of fixation between the substrate portion 20a and the cell culture membrane 15 and between the substrate portion 20b and the cell culture membrane 15 by temperature rising and pressing may be performed simultaneously or may be performed sequentially. In other words, the process of steps S110 and S120 may be performed simultaneously with regard to both the substrate portions 20a and 20b, or the process of steps S110 and S120 may be performed separately with regard to each of the substrate portions 20a and 20b.

According to the second embodiment, the sum of the thicknesses of the substrate portions 20a and 20b may be 0.05 to 0.5 mm. This configuration facilitates reinforcement of the cell culture membrane 15 by the substrate portions 20a and 20b and also enables cultured cells on the cell culture membrane 15 to be observed without detaching the cell culture membrane 15 from the substrate portions 20a and 20b after cell culture on the cell culture membrane 15 using the cell culture device 10. The sum of the thicknesses of the substrate portions 20a and 20b may, however, be less than 0.05 mm or may be greater than 0.5 mm.

C. Third Embodiment

Figure 8:
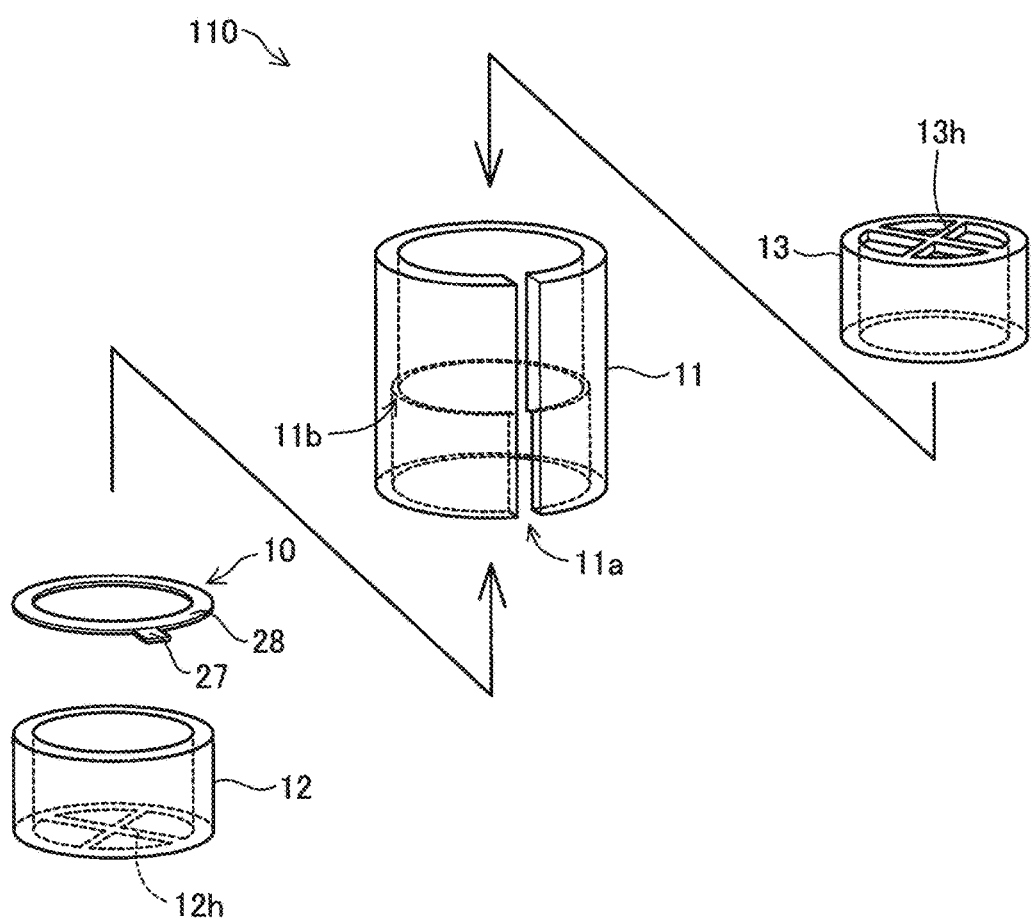
FIG. 8 is an exploded perspective view illustrating the configuration of a cell culture device according to a third embodiment.

FIG. 8 is an exploded perspective view illustrating the configuration of a cell culture device 110 according to a third embodiment. The cell culture device 110 of the third embodiment includes the cell culture device 10 of the first embodiment or the second embodiment. In the third embodiment, the like components to those of the first embodiment are expressed by the like reference numbers and are not described in detail. In the description of this embodiment, the cell culture device 10 of the first embodiment or the second embodiment is called cell culture membrane structure 10.

In a cell culture membrane 15 included in the cell culture membrane structure 10 of the third embodiment, at least part of pores 30 are formed as through holes. The cell culture device 110 of the third embodiment is a device used to seed cells on the respective surfaces of the cell culture membrane 15 for two-sided culture. The cell culture device 110 includes an outer cylinder 11, a first inner cylinder 12 and a second inner cylinder 13, in addition to the cell culture membrane structure 10.

The outer cylinder 11 is a tubular member having a slit 11a extended in an axial direction (height direction). The outer cylinder 11 may be made from, for example, a resin material or a rubber material. Since the outer cylinder 11 has the slit 11a in the height direction, the outer cylinder 11 may be made from a material that is elastically deformable in the radial direction. A step 11b is provided in the middle in the height direction of the inner wall of the outer cylinder 11 to have an abruptly changing diameter in a cross section perpendicular to the axial direction.

The first inner cylinder 12 is a tubular member formed to have a lower height than the height of the outer cylinder 11. The diameter of the first inner cylinder 12 in the cross section perpendicular to the axial direction of the outer cylinder 11 is substantially the same as the outer diameter of a frame body 28 of the cell culture membrane structure 10. A first grip 12h is provided at one end of the first inner cylinder 12 to cross an opening at this one end and link different locations on the outer circumference of the opening with each other. More specifically, the first grip 12h is formed from two linear members that are arranged to cross each other on an axial line of the first inner cylinder 12, i.e., that are arranged in a cross shape in the top view. The first inner cylinder 12 may be made from, for example, a resin material or a glass material. The first inner cylinder 12 may be a member having rigidity that suppresses substantial deformation when the first inner cylinder 12 is placed in the outer cylinder 11 and receives a force applied radially inward from the inner wall surface of the outer cylinder 11.

The second inner cylinder 13 is a tubular member formed to have a slightly smaller outer diameter than the outer diameter of the first inner cylinder 12 and have a lower height than the height of the outer cylinder 11. The second inner cylinder 13 may be made from the same material as that of the first inner cylinder 12. A second grip 13h similar to the first grip 12h of the first inner cylinder 12 is provided at one end of the second inner cylinder 13.

The cell culture device 110 is soaked in a culture solution when being used for cell culture. The outer cylinder 11, the first inner cylinder 12 and the second inner cylinder 13 may thus be made from a material that does not cause a substance likely to affect cultured cells (for example, component such as metal ion) to be substantially eluted in the culture solution. It is also desirable to make the outer cylinder 11, the first inner cylinder 12 and the second inner cylinder 13 from a material having a specific gravity that does not cause the cell culture device 110 to be floated in the culture solution. When the outer cylinder 11, the first inner cylinder 12 and the second inner cylinder 13 are made from a resin, the resin may be selected from the group consisting of, for example, polyethylene, polypropylene (PP), silicone resin, polytetrafluoroethylene (PTFE), polyethylene terephthalate (PET), polybutylene terephthalate (PET) and poly(methyl methacrylate) (PMMA).

FIG. 8 also illustrates a process of assembling the cell culture device 10 from the outer cylinder 11, the first inner cylinder 12, the second inner cylinder 13 and the cell culture membrane structure 10. Assembling the cell culture device 110 starts to place the cell culture membrane structure 10 on the other end of the first inner cylinder 12 (i.e., end without the first grip 12h).

Subsequently the first inner cylinder 12 integrated with the cell culture membrane structure 10 is inserted, from the side of the other end with the cell culture membrane structure 10 placed thereon, into the outer cylinder 11 through a larger-diameter opening of the outer cylinder 11. The first inner cylinder 12 is inserted such that a projection 27 of the cell culture device 110 is protruded radially outward from the slit 11a of the outer cylinder 11. The first inner cylinder 12 is inserted into the outer cylinder 11 until the frame body 28 of the cell culture membrane structure 10 placed on the first inner cylinder 12 comes into contact with the step 11b provided on the inner wall of the outer cylinder 11. The entire first inner cylinder 12 is accordingly placed in the outer cylinder 11. The outer diameter of the first inner cylinder 12 is made larger than the inner diameter of the outer cylinder 11 prior to such insertion. In the process of inserting the first inner cylinder 12 into the outer cylinder 11, the slit 11a is opened to elastically deform the outer cylinder 11 radially outward. This produces a gripping force applied radially inward from the outer cylinder 11 toward the first inner cylinder 12, so that the first inner cylinder 12 is tightly fit in the outer cylinder 11. While the first inner cylinder 12 is held in the outer cylinder 11, the cell culture membrane structure 10 is held between the step 11b on the inner wall of the outer cylinder 11 and one end of the first inner cylinder 12. The outer cylinder 11 fit on the outside of the first inner cylinder 12 holds the first inner cylinder 12 with such a gripping force that does not change the relative position of the first inner cylinder 12 in the outer cylinder 11 even when the cell culture device 110 is turned upside down.

Subsequently the second inner cylinder 13 is inserted, from the side of the other end without the second grip 13h, into the outer cylinder 11 through a smaller-diameter opening of the outer cylinder 11. The second inner cylinder 13 is inserted into the outer cylinder 11 until a leading end of the second inner cylinder 13 in the insertion direction comes into contact with the cell culture membrane structure 10 placed in the outer cylinder 11. Such insertion of the second inner cylinder 13 causes one end of the second inner cylinder 13 with the second grip 13h to be away from the smaller-diameter opening of the outer cylinder 11 through which the second inner cylinder 13 is inserted (as shown in FIG. 9A described later). The outer diameter of the second inner cylinder 13 is made larger than the inner diameter of the outer cylinder 11 prior to such insertion. The size of the step 11b is set to be substantially equal to a difference between the outer diameter of the first inner cylinder 12 and the outer diameter of the second inner cylinder 13. When the second inner cylinder 13 is inserted into the outer cylinder 11, the second inner cylinder 13 is accordingly held with a gripping fore applied radially inward from the outer cylinder 11, like the first inner cylinder 12.

When the assembled cell culture device 110 is used for cell culture, the cell culture device 110 is placed in a well of a plate for cell culture, and the well is filled with a culture solution.

FIGS. 9A to 9C are sectional diagrams illustrating two-sided culture using the cell culture device 110. FIG. 9A schematically illustrates the state that cells α are seeded on one surface of the cell culture membrane 15 (i.e., surface exposed on the outside of the first inner cylinder 12). A culture solution and a well of a plate for cell culture are omitted from the illustration of FIGS. 9A to 9C. A procedure of seeding the cells α on one surface of the cell culture membrane 15 may soak the cell culture device 110 in the culture solution such that this one surface of the cell culture membrane 15 faces up in the vertical direction and then supply a predetermined amount of the cells α into a space over this one surface in the second inner cylinder 13.

FIG. 9B illustrates the state that the second inner cylinder 13 is pulled up in a height direction (i.e., pulled up in the vertical direction) from the state of FIG. 9A to be away from the cell culture membrane structure 10. The second inner cylinder 13 can be readily pulled up by holding the second grip 13h. FIG. 9C illustrates the state that the cell culture device 110 is turned upside down from the state of FIG. 9B and that cells β are additionally seeded on a rear face opposite to the culture surface for the cells α. The cell culture device 110 is readily turned upside down by holding the first grip 12h and suspending the cell culture device 110.

According to this embodiment, the second inner cylinder 13 is configured to be slid in the height direction in the outer cylinder 11 and held at the slid position by applying an upward force in the height direction to the second inner cylinder 13 while holding the outer cylinder 11. This configuration may be provided by adjusting the size of the step 11b, the surface roughness of the inner wall surface of the outer cylinder 11 and the surface roughness of the outer surface of the second inner cylinder 13, the weight of the second inner cylinder 13, and the like.

The slit 11a provided on the outer cylinder 11 is extended in the axial direction to pass through the position where the cell culture device 110 is placed. When the second inner cylinder 13 is pulled up to be away from the cell culture membrane structure 10 as shown in FIG. 9B, the space over the culture surface of the cell culture membrane 15 for the cells α communicates with outside of the outer cylinder 11 via the slit 11a in the neighborhood of the culture surface for the cells α. This configuration enables the air to be readily released from the culture surface for the cells α through the slit 11a when the cell culture device 110 is turned upside down. The state of the air release is shown by an arrow in FIG. 9C. This suppresses a potential problem caused by the air remaining on the culture surface for the first seeded cells α (for example, a failure to expose the cells α to the culture solution).

This embodiment uses the cell culture device 110 including the porous membrane having a large number of through holes that are formed to pass through in the thickness direction, as the cell culture membrane 15. This configuration enables different types of cells to be cultured on the respective surfaces of the cell culture membrane for the purpose of analysis of interactions between the different types of cells. The different types of cells can be readily seeded on the respective surfaces of the cell culture membrane 15 by simply turning the cell culture device 110 upside down.

The respective components constituting the cell culture device 110 are assembled and integrated by engagement, so that the cell culture device 110 can be assembled by the simple operation such as insertion. Additionally, the respective components to be assembled are neither bonded to each other by using an adhesive nor fixed to each other by welding. The respective components can thus be readily disassembled by releasing the engagement. This facilitates detachment of the cell culture membrane structure 10 for the purpose of observation of cultured cells. This configuration also protects the respective components from being damaged by disassembly of the cell culture device 110. The first inner cylinder 12, the second inner cylinder 13 and the outer cylinder 11 disassembled from the cell culture device 110 after cell culture can be readily reused.

The "engagement" herein means the state that the positions of the respective components are fixed to each other during cell culture without fixing the components to each other via another substance such as an adhesive and without mixing constituent materials of the respective components in a contact region between the components such as welding. Concrete examples of such engagement include assembly using the concavo-convex structure such as the step 11b and assembly using the elastic force produced in the outer cylinder 11 having the slit 11a as described in the third embodiment. According to a modification, the respective components of the cell culture device including the cell culture membrane structure 10 may, however, be integrated by a method other than "engagement", for example, a method using an adhesive.

The first inner cylinder 12, the second inner cylinder 13 and the outer cylinder 11 of this embodiment correspond to the "base" described in SUMMARY.

Figure 10A:
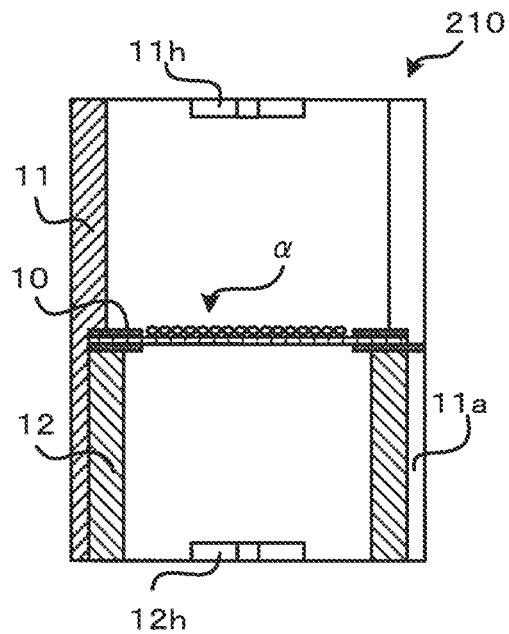
FIGS. 10A and 10B are sectional diagrams illustrating the schematic configurations of cell culture devices according to modifications of the third embodiment.
Figure 10B:
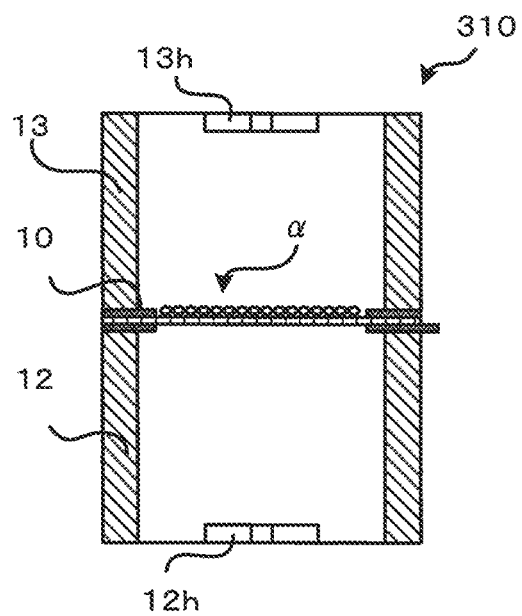

FIGS. 10A and 10B are sectional diagrams illustrating the schematic configurations of cell culture devices 210 and 310 suitable for two-sided culture according to modifications of the third embodiment. The cell culture device 210 shown in FIG. 10A differs from the cell culture device 110 by omitting the second inner cylinder 13 and providing the outer cylinder 11 with a third grip 11h like the second grip 13h. This configuration causes the cell culture membrane structure 10 to be held between the first cylinder 12 and the step 11b of the outer cylinder 11 by engagement and has similar advantageous effects to those of the third embodiment.

The cell culture device 310 shown in FIG. 10B differs from the cell culture device 110 by omitting the outer cylinder 11 and holding the cell culture membrane structure 10 to be placed between the first inner cylinder 12 and the second inner cylinder 13 stacked each other. In the cell culture device 310, the diameters in the cross sections of the first inner cylinder 12 and the second inner cylinder 13 are made substantially equal to the outer diameter of the frame body of the culture membrane structure 10. Employing, for example, glass members for the first inner cylinder 12 and the second inner cylinder 13 provides the inner cylinders 12 and 13 having the sufficient weight and thereby ensures the sufficient sealability between the respective inner cylinders 12 and 13 and the frame body of the cell culture membrane structure 10. This configuration causes the cell culture membrane structure 10 to be held between the first inner cylinder 12 and the second inner cylinder 13 and has similar advantageous effects to those of the third embodiment.

D. Fourth Embodiment

Figure 11:
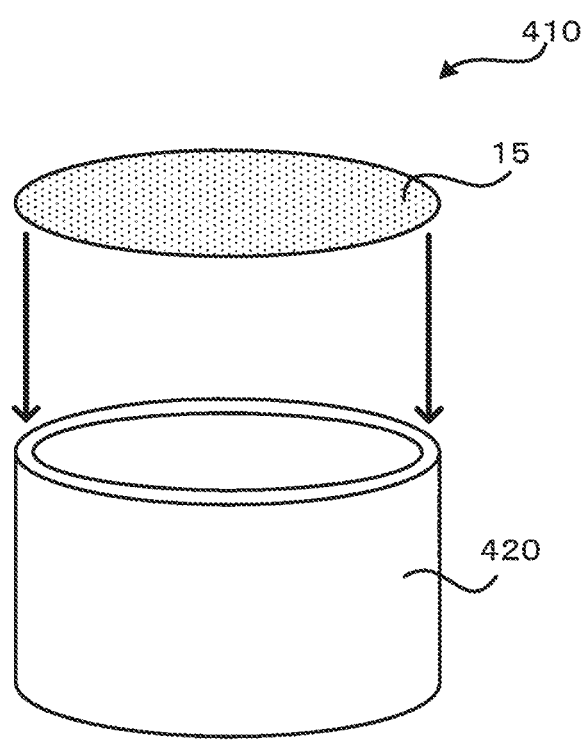
FIG. 11 is an exploded perspective view illustrating the schematic configuration of a cell culture device according to a fourth embodiment.

FIG. 11 is an exploded perspective view illustrating the schematic configuration of a cell culture device 410 according to a fourth embodiment. In the fourth embodiment, the like components to those of the first embodiment are expressed by the like reference numbers and are not described in detail. The cell culture device 410 includes a cell culture membrane 15 and a substrate 420.

The substrate 420 is a tubular member and is made from a thermoplastic resin similar to that used for the substrate 20 of the first embodiment. The substrate 420 has a ring-shaped cross section perpendicular to an axial direction. The outer diameter of this cross section is made substantially equal to the outer diameter of the cell culture membrane 15. In order to manufacture the cell culture device 410, the cell culture membrane 15 is placed on the substrate 420 such as to close an opening at one end of the substrate 420. Like the first embodiment, the surface of the substrate 420 is melted or softened by temperature rising, and the cell culture membrane 15 stacked on the substrate 420 is pressed against the substrate 420 so as to be fixed to the substrate 420. The cell culture membrane 15 may not necessarily have through holes provided as pores 30. The cell culture membrane 15 is placed on the substrate 420 such that a surface of the cell culture membrane 15 to which the pores 30 are open is in contact with the substrate 420. This configuration causes bulges 25 to be formed in the pores 30 of the cell culture membrane 15 by extending part of the substrate 420. In use, the cell culture device 410 may be placed in a well of a plate for cell culture, such that the side of the substrate 420 with the cell culture membrane 15 fixed thereto faces down. In this state, the surface of the cell culture membrane 15 to which the pores 30 are open faces up in the substrate 420. The space over the cell culture membrane 15 in the substrate 420 may be filled with a culture solution, and desired cells may be seeded on the surface of the cell culture membrane 15. The cell culture device 410 may be used for such one-sided culture. This configuration has similar advantageous effects to those of the first embodiment.

FIGS. 12A to 12C are sectional diagrams illustrating application of a cell culture device 510 according to a modification of the fourth embodiment, like FIGS. 9A to 9C. In the modification of the fourth embodiment, like components to those of the first embodiment or the third embodiment are expressed by the like reference numbers and are not described in detail.

The cell culture device 510 includes the cell culture device 410 of the fourth embodiment. In the description of this modification, the cell culture device 410 of the fourth embodiment is called cell culture membrane structure 410. In the cell culture device 510, the cell culture membrane 15 of the cell culture membrane structure 410 has through holes provided as pores 30.

The cell culture device 510 is a device used for two-sided culture and has a configuration similar to the cell culture device 110 of the third embodiment except that the cell culture membrane structure 410 is provided in place of the cell culture membrane structure 10 and the first inner cylinder 12. An outer cylinder 11 of the cell culture device 510 has an approximately constant inner diameter at its cross section and does not have the step 11b.

As shown in FIGS. 12A to 12C, the cell culture device 510 including the cell culture membrane structure 410 in place of the first inner cylinder 12 and the cell culture membrane structure 10 shown in FIGS. 9A to 9C may be used for two-sided culture by series of operations similar to those described above with reference to FIGS. 9A to 9C. This configuration has similar advantageous effects to those of the first and the third embodiments.

The configuration using the cell culture membrane structure 410 in place of the cell culture membrane structure 10 and the first inner cylinder 12 of the third embodiment may be applied to either of the configurations of FIGS. 10A and 10B according to the modifications of the third embodiment. For example, a cell culture device may be configured by placing only the cell culture membrane structure 410 in the outer cylinder 11 with omission of the second inner cylinder 13. In another example, a cell culture device for two-sided culture may be configured by stacking the cell culture membrane structure 410 and the second inner cylinder 13 each other with omission of the outer cylinder 11.

The above configuration using the cell culture membrane structure 410 can reduce the total number of components constituting the cell culture device, compared with the configuration of the third embodiment using the cell culture membrane structure 10 and the first inner cylinder 12. The configuration of the third embodiment, however, includes the substrate 20 provided as the ring-shaped member separate from the first inner cylinder 12. This configuration increases the flexibility of selection for the material of the first inner cylinder 12 without taking into account the melting point or the softening point of the substrate 20 and enables the cell culture membrane 15 from being readily detached from the tubular member for observation.

E. Fifth Embodiment

Figure 13A:
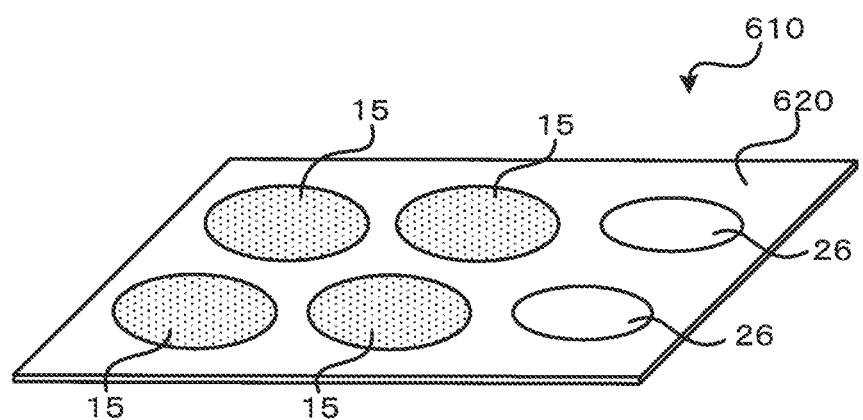
FIGS. 13A and 13B are perspective views schematically illustrating the appearance of a cell culture device according to a fifth embodiment.
Figure 13B:
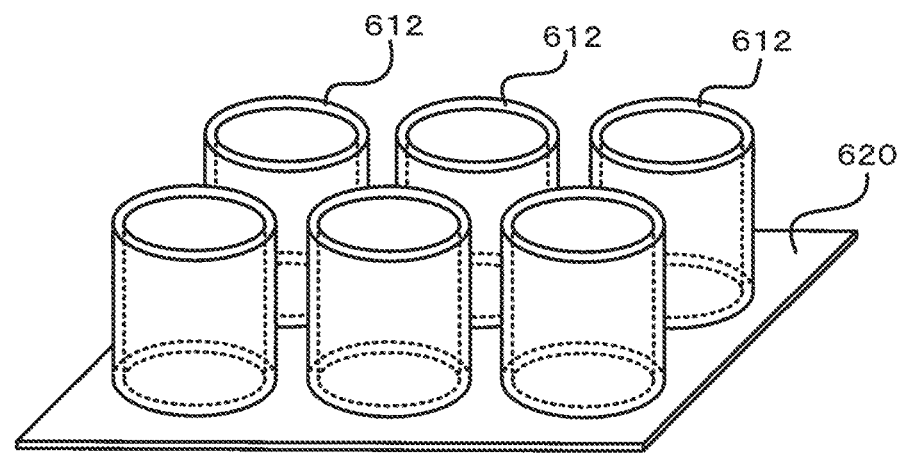

FIGS. 13A and 13B are perspective views schematically illustrating the appearance of a cell culture device 610 according to a fifth embodiment. In the fifth embodiment, the like components to those of the first embodiment are expressed by the like reference numbers and are not described in detail. As shown in FIG. 13A, the cell culture device 610 includes a plurality of cell culture membranes 15 and a substrate 620.

The substrate 620 is a plate-like member and is made from a thermoplastic resin similar to that used for the substrate 20 of the first embodiment. The substrate 620 has a plurality of holes 26 formed in a circular shape in the plan view to pass through the substrate 620 in the thickness direction. The outer diameter of each of the holes 26 is made slightly smaller than the outer diameter of the cell culture membrane 15. In order to manufacture the cell culture device 610, the cell culture membranes 15 are placed on the respective holes 26 to close the respective holes 26 of the substrate 620. Like the first embodiment, contact regions of the substrate 620 that are in contact with the cell culture membranes 15 are melted or softened by temperature rising, and the cell culture membranes 15 stacked on the substrate 620 are pressed against the substrate 620 to be fixed to the substrate 620. The cell culture membranes 15 may not necessarily have through holes provided as pores 30. The cell culture membranes 15 are placed on the substrate 620 such that respective surfaces of the cell culture membranes 15 to which the pores 30 are open are in contact with the substrate 620. This configuration causes bulges 25 to be formed in the pores 30 of the cell culture membranes 15 by extending part of the substrate 620. FIG. 13A illustrates the state in the middle of manufacture that the cell culture membranes 15 are fixed to close four holes 26 among six holes 26 provided in the substrate 620.

FIG. 13B illustrates one application using the cell culture device 610 for cell culture. In use, for example, the cell culture device 610 may be placed in a plate for cell culture, such that the surfaces of the cell culture membranes 15 to which the pores 30 are open face up. Tubular members 612 are then mounted on the cell culture device 610 to surround the respective cell culture membranes 15. The tubular member 612 is a cylindrical member having an inner circumference substantially equal to the outer circumference of the hole 26. The tubular member 612 is made from a material that does not cause a substance likely to affect cultured cells to be substantially eluted in a culture solution and has a weight to provide the sufficient sealability between the tubular member 612 and the substrate 620. For example, a glass member may be employed for the tubular member 612. The space over the cell culture membrane 15 in the substrate 620 may be filled with a culture solution, and desired cells may be seeded on the surface of the cell culture membrane 15. The cell culture device 610 may be used for such one-sided culture. This configuration has similar advantageous effects to those of the first embodiment.

When the sufficient sealability is ensures between the tubular members 612 and the substrate 620, different media may be used for cell culture in the respective cell culture membranes 15 exposed in the respective tubular members 612. The tubular members 612 may be integrated with the substrate 620 by a technique other than mounting the tubular members 612 on the substrate 620. Although the tubular members 612 may be fixed to the substrate 620 by a method other than mounting, mounting the tubular members 612 desirably facilitates detachment of the cell culture device 610 for observation of cultured cells. The thickness of the substrate 620 may be, for example, 0.05 to 0.5 μm. This configuration facilitates reinforcement of the cell culture membranes 15 by the substrate 620 and also enables cultured cells on the cell culture membranes 15 to be observed without detaching the cell culture membranes 15 from the substrate 620. The thickness of the substrate 620 may, however, be less than 0.05 mm or may be greater than 0.5 mm.

The plurality of tubular members 612 to be placed on the respective holes 26 may be integrated in advance to have a positional relationship corresponding to the positional relationship of the respective holes 26. The plurality of holes 26 may be collectively covered with a single cell culture membrane, instead of providing separate cell culture membranes 15 for the respective holes 26.

F. Modifications

Modification 1 (Modification of Manufacturing Method)

In the respective embodiments described above, the process of fixing the substrate to the cell culture membrane 15 at step S120 in FIG. 4 simultaneously performs the operation of raising the temperature of the substrate and the operation of pressing the stacked substrate and cell culture membrane 15 against each other. A different process may, however, be employed. For example, an area including the surface of a fixation region of the substrate may be melted or softened in advance by temperature rising, and the substrate and the cell culture membrane 15 may subsequently be placed in contact with each other and pressed against each other. Melting or softening the surface of the substrate during pressing allows for formation of the bulges 25 in the pores 30.

Modification 2 (Modification of Shape of Cell Culture Membrane)

The cell culture membrane 15 is formed in a circular shape in the respective embodiments described above, but may be formed in another shape. In this modification, the shape of the substrate may be set appropriately according to the shape of the cell culture membrane 15.

Modification 3 (Modification of Sheet-Like Substrate)

According to the second embodiment, the substrate is comprised of the substrate portions 20a and 20b provided as ring-shaped sheets. In the case of a sheet-like substrate, there is generally a difficulty in discriminating between the surface and the rear face of the cell culture device by the difference in shape. In the case of using the pair of sheet-like substrate portions like the second embodiment, the respective substrate portions may be provided to have different colors, in order to facilitate visual discrimination between the surface and the rear face of the cell culture device. For example, a method employed to provide substrate portions in different colors may color at least one of the substrate portions. A pigment that does not cause a substance likely to affect cultured cells to be substantially eluted from a substrate portion into a culture solution may be mixed with the substrate portion and used to color the substrate portion. The pigment usable for this purpose may be, for example, carbon.

Coloring the substrate 20 is not limited to the configuration of the substrate that consists of the pair of substrate portions like the second embodiment but may also be desirably applied to the configuration of the substrate 20 that is formed by a single sheet like the first embodiment, in order to enhance the visibility and allow for discrimination between the surface and the rear face of the cell culture device. For example, when the substrate 20 with the cell culture membrane 15 fixed to one surface thereof is made from a light-colored thermoplastic resin, it is generally difficult to discriminate between the surface and the rear face of the cell culture device by the color of the substrate 20. Coloring the substrate 20 in a deep color, however, causes the surface of the substrate 20 with the cell culture membrane 15 fixed thereto to be left in the light color. This facilitates discrimination between the surface and the rear face of the cell culture membrane 15 fixed to the substrate 20.

As long as visual discrimination is allowed between the surface and the rear face of the cell culture device, a technique other than coloring the substrate may be employed. For example, a specific concavo-concave structure may be formed on the surface of a substrate in a visible manner on one surface of the cell culture device. In another example, a plurality of through holes in visible sizes may be provided at asymmetric positions (to allow for discrimination between the surface and the rear face). In another example, asymmetric concave-concave structures may be provided on the outer circumference of the substrate.

Modification 4 (Modification of Shape of Substrate Portion)

According to the second embodiment, the substrate is comprised of the substrate portions 20a and 20b provided as ring-shaped sheets. According to a modification, the substrate may be configured by combining substrate portions in different shapes. For example, the substrate portion of the ring-shaped sheet used in the second embodiment may be combined with the substrate 420 in the tubular form used in the fourth embodiment. In this case, the cell culture membrane 15 with through holes may be placed between the substrate portion of the ring-shaped sheet and the tubular substrate portion, and the bulges 25 extended from the respective substrate portions may be formed in the pores 30 of the cell culture membrane 15 by heating and pressing. When a cell culture device is configured by placing a cell culture membrane between two substrate portions, the respective substrate portions may be made from one identical thermoplastic resin or may be made from different thermoplastic resins.

Both in the case of using the single substrate and in the case of using the pair of substrate portions to constitute the substrate, the shape of the substrate is not limited to the frame-like sheet or the tubular body but may any shape that reinforces the cell culture membrane 15. Any configuration that the substrate is made from a thermoplastic resin and the bulges 25 are provided in the pores 30 of the cell culture membrane 15 provides the similar advantageous effects to those of the respective embodiments described above.

EXAMPLES

FIG. 14 is a table showing results of a fixation test using a thermosetting resin membrane corresponding to the cell culture membrane and a thermoplastic resin member corresponding to the substrate. A membrane made from a thermosetting resin, polyurethane (PU), was used as the membrane corresponding to the cell culture membrane. The following describes the results of the fixation test with regard to eight samples, sample 1 to sample 8.

<Polyurethane Porous Membrane>

A polyurethane porous membrane was manufactured as described below. In manufacture of a polyurethane porous membrane, the polyol used was polyether polyol (polypropylene ethylene polyol (PPG) having the number-average molecular weight of about 4000 and the hydroxyl value of 37). The isocyanate used was polyol-modified diphenyl methane diisocyanate (MDI) containing 28.0% by mass of isocyanate group (NCO) at the molecular end. The cross-linking agent used as diethylene glycol (DEG). The diluting solvent used was tetrahydrofuran (THF). The modified used was water or more specifically ultrapure water (Milli-Q water).

A layer of an uncured polyurethane raw material consisting of these raw materials was formed on a polypropylene (PP) film used as a base plate for membrane formation by spin coating method. A polyurethane porous membrane was then manufactured by curing the layer of the polyurethane raw material with supplying water vapor to the layer of the uncured polyurethane raw material.

The water vapor was supplied to the layer of the uncured polyurethane raw material as described below. A closed container containing water was placed in a thermostatic oven set at a curing temperature (for example, 60° C.) and was heated until the temperature of water included in the closed container reached the curing temperature. The layer of the uncured polyurethane raw material formed on the base plate for membrane formation was subsequently fixed to the rear side of a cover of the closed container and was arranged to face water in the closed container. The closed container was then placed back in the thermostatic oven, so that the layer of the uncured polyurethane raw material was subjected to a curing reaction while being exposed to saturated water vapor at the curing temperature.

The shape of the polyurethane porous membrane may be controlled by adjusting conditions selected among the reaction temperature and the reaction time in the curing reaction for manufacturing the polyurethane porous membrane and the composition of the polyurethane raw material. More specifically the diameter of pores, the depth of pores (whether at least part of the pores are through holes) or the shape of pores may be changed by changing these conditions. Various polyurethane porous membranes were manufactured by changing these conditions. The membrane thickness and the average pore diameter were measured, and the shape of pores and the presence or the absence of through holes were checked with regard to each polyurethane porous membrane obtained. Polyurethane porous membranes having the membrane thickness of 20 to 30 μm and the average pore diameter of 5 to 15 μm were selected and used as polyurethane porous membranes of respective samples.

In the description below, the polyurethane porous membrane with through holes substantially formed as the pores is called two-sided membrane. The polyurethane porous membrane without through holes substantially formed as the pores is called one-sided membrane. More specifically, the section of the polyurethane porous membrane manufactured was observed at 1000-fold magnification with a scanning electron microscope (SEM). The membrane in which 10% or more of the total number of the pores were through holes was called two-sided membrane. The membrane in which less than 10% of the total number of the pores were through holes was called one-sided membrane. Samples 1 to 4 and 6 used one-sided membranes. Samples 7 and 8 used two-sided membranes. Sample 5 used a membrane with no formation of pores (flat membrane) manufactured without supplying water vapor during curing of the layer of the uncured polyurethane raw material.

[Sample 1]

Sample 1 used a one-sided membrane as the polyurethane porous membrane as described above. After manufacture of the polyurethane porous membrane, the base plate for membrane formation was detached from the polyurethane porous membrane. A polyethylene terephthalate (PET) member was used as a substrate and was stacked on and fixed to a surface of the one-sided membrane to which the pores were open. A process of fixing the polyurethane membrane and the substrate to each other is hereinafter referred to as "fixation process". The stacked structure of the polyurethane membrane and the substrate after the fixation process is called "stacked body" in the description below.

Figure 15:
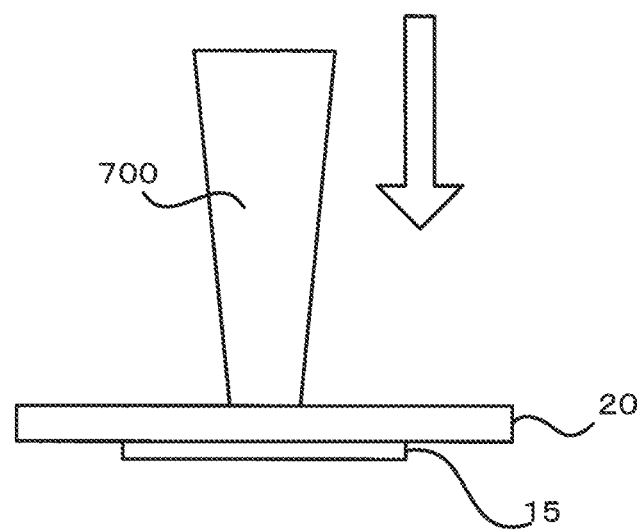
FIG. 15 is a diagram schematically illustrating the state of fixation of a polyurethane porous membrane to a substrate.

FIG. 15 is a diagram schematically illustrating the state of fixation of a polyurethane porous membrane (cell culture membrane 15) to a substrate (substrate 20). A ultrasonic welding machine was used for the fixation process, and a horn 700 (φ=5 mm) was placed on and pressed against the substrate 20. Heat was applied from the substrate 20-side on which the horn 700 was placed. The direction of applying a load is shown by open arrow in FIG. 15. The conditions of the fixation process were the load of 300 g applied by the horn 700, the electric current of 3 mA and the time of 10 seconds.

The state of fixation was evaluated by a peeling test and section observation. In the peeling test, the polyurethane porous membrane was peeled from the stacked body after the fixation process. When the polyurethane porous membrane was peeled off without any damage, this indicates that the polyurethane porous membrane was not sufficiently fixed to the substrate. The evaluation result was accordingly "x" (cross mark). When the polyurethane porous membrane was not peeled off without any damage, this indicates that the polyurethane porous membrane was sufficiently fixed to the substrate. The evaluation result was accordingly "o" (circle mark).

In the section observation, a section of a connection region between the polyurethane porous membrane and the substrate was observed at 1000-fold magnification with a scanning electron microscope (SEM). It was then determined whether the state that "bulges 25 were formed in the pores 30 of the cell culture membrane 15" described above was satisfied with regard to the observed section. When this state was satisfied, this indicates that the bulges 25 were formed in the pores 30, so that the polyurethane porous membrane was sufficiently fixed to the substrate. The evaluation result was accordingly "o". When this state was not satisfied, this indicates that the bulges 25 were not formed in the pores 30, so that the polyurethane porous membrane was not sufficiently fixed to the substrate. The evaluation result was accordingly "x".

In Sample 1, the evaluation results of both the peeling test and the section observation were "o". This indicates the good fixation.

Figure 16:
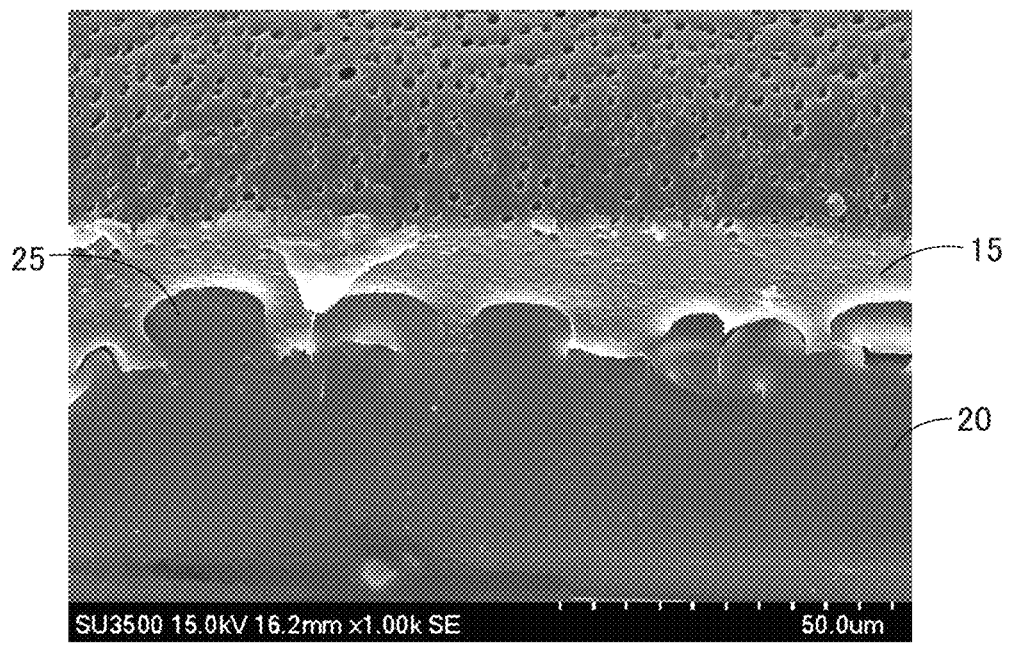
FIG. 16 is an image showing the result of observation of a section of a stacked body of a polyurethane porous membrane and a substrate in Sample 1.

FIG. 16 is an image showing the result of observation of a section of the stacked body of Sample 1 as one example of the state of fixation of the polyurethane porous membrane to the substrate. More specifically, FIG. 16 shows the result of observation at 1000-fold magnification at an accelerating voltage of 15 kV with a scanning electron microscope (SEM, S-800 manufactured by Hitachi, Ltd. In the image of FIG. 16, the section of the stacked body is observed obliquely downward. The image includes the surface of the polyurethane porous membrane after detachment from the base plate for membrane formation shown in the upper portion of the image, in addition to the section of the stacked body. The observation result of FIG. 16 shows that bulges 25 are extended from the substrate 20 to be formed in the pores of the polyurethane porous membrane (cell culture membrane 15).

[Sample 2]

In Sample 2, the fixation process was performed similarly to that of Sample 1 except that the load applied by the horn 700 was 500 g and the time was 5 seconds. Sample 2 was subjected to the peeling test and the section observation similar to those of Sample 1. In Sample 2, the evaluation results of both the peeling test and the section observation were "o".

[Sample 3]

In Sample 3, the fixation process was performed similarly to that of Sample 1 except that the load applied by the horn 700 was 900 g, the electric current was 2 mA and the time was 5 seconds. Sample 3 was subjected to the peeling test and the section observation similar to those of Sample 1. In Sample 3, the evaluation results of both the peeling test and the section observation were "o".

[Sample 4]

In Sample 4, the fixation process was performed similarly to that of Sample 1 except that the load applied by the horn 700 was 450 g, the electric current was 2 mA and the time was 5 seconds. Sample 4 was subjected to the peeling test and the section observation similar to those of Sample 1. In Sample 4, the evaluation results of both the peeling test and the section observation were "x".

[Sample 5]

Unlike Samples 1 to 4, the polyurethane membrane used was a flat membrane in Sample 5 as described above. In Sample 5 the fixation process was performed similarly to that of Sample 1 except that the load applied by the horn 700 was 500 g. In Sample 5, the evaluation result of the peeling test performed similarly to that of Sample 1 was "x". The polyurethane membrane of Sample 5 was a flat membrane without pores, so that Sample 5 was not subjected to the section observation.

[Sample 6]

In Sample 6, the fixation process was performed similarly to that of Sample 1 except that a polypropylene (PP) member was used as a substrate, the load applied by the horn 700 was 200 g, the electric current was 2 mA and the time was 3 seconds. Sample 3 was subjected to the peeling test and the section observation similar to those of Sample 1. In Sample 3, the evaluation results of both the peeling test and the section observation were "o".

[Sample 7]

A two-sided membrane was used as the polyurethane porous membrane in Sample 7 as described above. In Sample 7, after manufacture of the polyurethane porous membrane, the base plate for membrane formation was not detached from the polyurethane porous membrane, and a member used for a substrate was stacked on and fixed to a different surface of the polyurethane porous membrane that was opposite to the surface in contact with the base plate for membrane formation. A polypropylene (PP) member was used for the substrate. The stacked structure of the base plate for membrane formation, the polyurethane membrane and the substrate after the fixation process is called "stacked body" in the description below.

An ultrasonic welding technique was employed for the fixation process of Sample 7, like those of Sample 1 to 6, but the ultrasonic welding of Sample 7 was manually performed without an ultrasonic welding machine. The load as a fixation condition was accordingly unknown. The other fixation conditions were the electric current of 3 mA and the time of 10 seconds. Sample 7 was subjected to the section observation similar to that of Sample 1. In the peeling test, the substrate was peeled from the stacked body after the fixation process. When the substrate was peeled off without damaging the polyurethane porous membrane, this indicates that the polyurethane porous membrane was not sufficiently fixed to the substrate. The evaluation result was accordingly "x" (cross mark). When the substrate was stuck and was not peeled off without damaging the polyurethane porous membrane, this indicates that the polyurethane porous membrane was sufficiently fixed to the substrate. The evaluation result was accordingly "o" (circle mark). In Sample 7, the evaluation results of both the peeling test and the section observation were "o".

Figure 17:
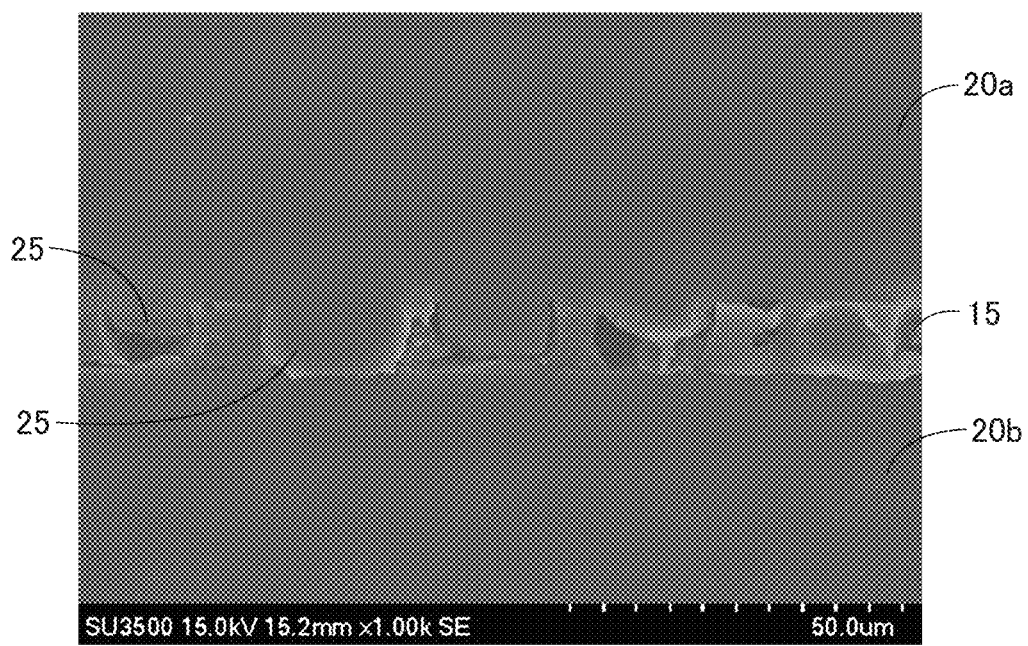
FIG. 17 is an image showing the result of observation of a section of a stacked body of a polyurethane porous membrane and a substrate in Sample 7.

FIG. 17 is an image showing the result of observation of a section of the stacked body of Sample 7 as one example of the state of fixation of the polyurethane porous membrane to the substrate. More specifically, FIG. 17 shows the result of observation at 1000-fold magnification at an accelerating voltage of 15 kV with a scanning electron microscope (SEM, S-800 manufactured by Hitachi, Ltd. The observation result of FIG. 17 shows that bulges 25 are extended from the substrate to be formed in the pores of the polyurethane porous membrane (cell culture membrane 15). In FIG. 17, a substrate portion 20*a* denotes the member placed as the substrate on the polyurethane porous membrane in the fixation process, and a substrate portion 20*b* denotes the base plate for membrane formation. As shown in FIG. 17, in the stacked body of Sample 7, the bulge 25 extended from the substrate portion 20*a* passes through the pore and reaches the surface of the substrate portion 20*b*, so that the substrate portion 20*a* and the substrate portion 20*b* are connected with each other.

[Sample 8]

A two-sided membrane was used as the polyurethane porous membrane in Sample 8 as described above. In Sample 8, after manufacture of the polyurethane porous membrane, the base plate for membrane formation was not detached from the polyurethane porous membrane, and a member used for a substrate was stacked on and fixed to a different surface of the polyurethane porous membrane that was opposite to the surface in contact with the base plate for membrane formation. A polypropylene (PP) member was used for the substrate.

In Sample 8, the fixation process heated and previously melted the member used for the substrate at 235° C. higher than the melting point of polypropylene, placed the substrate in the melted state on the polyurethane porous membrane, and pressed and cooled down the entire stacked body. In Sample 8, the evaluation result of the peeling test performed similarly to that of Sample 6 was "o". Sample 8 was not evaluated by the section observation. According to the results of the evaluation with regard to the other samples, the result of the peeling test agrees well with the result of the section observation. In Sample 8, it is accordingly expected that bulges are extended from the substrate to be formed in the pores.

According to the results of FIG. 14, the porous membrane and the substrate can be firmly fixed to each other by stacking and pressing the substrate in the surface melted or softened state on and against the porous membrane made from the thermosetting resin to form bulges extended from the substrate into the pores of the porous membrane. In Sample 4, the result of the section observation indicates no formation of bulges, and the result of the peeling test indicates insufficient fixation. This may attributed to that the insufficient temperature rising of the surface of the substrate under some fixation conditions specified by the load, the electric current and the time fails to sufficiently melt or soften the thermoplastic resin on the surface of the substrate and accordingly fails to extend the substrate into the pores of the porous membrane. The fixation conditions of Sample 6 were the smaller load and the shorter time than the fixation conditions of Sample 4. The evaluation results of both the peeling test and the section observation in Sample 6 were, however, "o", unlike Sample 4. This may be attributed to that the melting point of the thermoplastic resin used to form the substrate in Sample 6 is lower than that in Sample 4 and that even the lower temperature to which the temperature of the surface of the substrate is raised allows for formation of bulges by extending the substrate into the pores. This indicates that selecting a resin having a lower melting point as the thermoplastic resin used to form the substrate allows for fixation by formation of the bulges in the pores of the porous membrane even at the lower temperature to which the temperature of the surface of the substrate is raised in the fixation process.

The disclosure is not limited to any of the embodiments, the examples and the modifications described above but may be implemented by a diversity of other configurations without departing from the scope of the disclosure. For example, the technical features of any of the embodiments, the examples and modifications corresponding to the technical features of each of the aspects described in Summary may be replaced or combined appropriately, in order to solve part or all of the problems described above or in order to achieve part or all of the advantageous effects described above. Any of the technical features may be omitted appropriately unless the technical feature is described as essential herein.

What is claimed is:

1. A cell culture device comprising:
   a cell culture membrane; and
   a reinforcement substrate fixed to the cell culture membrane, wherein
   the cell culture membrane is made from a thermosetting resin and has a plurality of pores that are open to at least one surface including a surface on a side that is in contact with the substrate,
   the reinforcement substrate is made from a thermoplastic resin,
   in a contact region between the cell culture membrane and the reinforcement substrate, part of the reinforcement substrate extends to form bulges in the pores of the cell culture membrane that are open in the contact region, and
   the cell culture membrane has a thickness of 0.1 to 100 µm.

2. The cell culture device according to claim 1, wherein the thermosetting resin from which the cell culture membrane is made is polyurethane.

3. The cell culture device according to claim 1, wherein the thermoplastic resin from which the substrate is made is a resin selected from the group consisting of polyethylene, polypropylene, polystyrene, AS resin, ABS resin, polyvinyl chloride, acrylic resin, polyethylene terephthalate, polybutylene terephthalate, polyvinyl alcohol, polyvinylidene fluoride, nylon 6, nylon 66, nylon 12, polyacetal, polycarbonate, polyether imide, polysulfone, polychlorotrifluoroethylene and polylactic acid.

4. The cell culture device according to claim 1, wherein the cell culture membrane has an average pore diameter of 0.1 to 100 µm in the surface on the side that is in contact with the substrate.

5. The cell culture device according to claim 1, wherein the reinforcement substrate is a ring-shaped sheet having a thickness of 0.05 to 0.5 mm and including a ring-shaped frame body, and
   the cell culture membrane is fixed to the frame body of the reinforcement substrate such as to close an opening of the ring-shaped sheet.

6. The cell culture device according to claim 5, further comprising:
   a base that is configured to hold the reinforcement substrate, wherein
   the reinforcement substrate and the base are assembled by engagement.

7. The cell culture device according to claim 1,
   wherein at least part of the plurality of pores included in the cell culture membrane are through holes formed to pass through the cell culture membrane in a membrane thickness direction,
   the reinforcement substrate is made from the thermoplastic resin and comprises a first substrate portion placed on a first surface of the cell culture membrane and a second substrate portion placed on a second surface of the cell culture membrane,
   the contact region includes a first contact region in which the first substrate portion comes into contact with the first surface of the cell culture membrane and a second contact region in which the second substrate portion comes into contact with the second surface of the cell culture membrane, and
   in both the first contact region and the second contact region, part of the first substrate portion and part of the second substrate portion are extended to form bulges in the pores of the cell culture membrane that are open in either of the first and the second contact regions.

8. The cell culture device according to claim 1,
   wherein at least part of the plurality of pores included in the cell culture membrane are through holes formed to pass through the cell culture membrane in a membrane thickness direction,
   the reinforcement substrate is made from the thermoplastic resin and comprises a first substrate portion placed on a first surface of the cell culture membrane and a second substrate portion placed on a second surface of the cell culture membrane,
   the contact region includes a first contact region in which the first substrate portion comes into contact with the first surface of the cell culture membrane and a second contact region in which the second substrate portion comes into contact with the second surface of the cell culture membrane, and
   the first substrate portion and the second substrate portion are connected with each other by bulges that are extended from at least one of the first substrate portion and the second substrate portion via the through holes formed in the cell culture membrane to be open in the first and the second contact regions.

9. The cell culture device according to claim 1, wherein the reinforcement substrate is welded to the cell culture membrane.

10. The cell culture device according to claim 1, wherein the reinforcement substrate is press-fitted into the cell culture membrane.

11. The cell culture device according to claim 1, wherein the reinforcement substrate includes a body and a handle that projects from the body of the reinforcement substrate.

12. The cell culture device according to claim 11, wherein the body of the reinforcement substrate conforms to a profile of the cell culture membrane, and the handle projects beyond the profile of the cell culture membrane.

* * * * *